(12) United States Patent
Glidden

(10) Patent No.: US 7,691,839 B2
(45) Date of Patent: Apr. 6, 2010

(54) METHODS AND COMPOSITIONS FOR BLOCKING PLATELET AND CELL ADHESION, CELL MIGRATION AND INFLAMMATION

(75) Inventor: Paul F. Glidden, San Diego, CA (US)

(73) Assignee: Biovascular, Inc., La Jolla, CA (US)

( * ) Notice: Subject to any disclaimer, the term of this patent is extended or adjusted under 35 U.S.C. 154(b) by 179 days.

(21) Appl. No.: 11/540,203

(22) Filed: Sep. 28, 2006

(65) Prior Publication Data

US 2007/0099819 A1 May 3, 2007

Related U.S. Application Data

(60) Provisional application No. 60/721,754, filed on Sep. 28, 2005.

(51) Int. Cl.
A61K 31/33 (2006.01)
A61K 38/00 (2006.01)
A61F 2/00 (2006.01)

(52) U.S. Cl. .......................... 514/183; 514/12; 424/423

(58) Field of Classification Search .................. 514/579
See application file for complete search history.

(56) References Cited

U.S. PATENT DOCUMENTS

| | | | |
|---|---|---|---|
| 4,767,742 A | 8/1988 | Dodt et al. |
| 5,139,944 A | 8/1992 | Sawyer et al. |
| 5,179,082 A | 1/1993 | Connolly et al. |
| 5,182,260 A | 1/1993 | Maraganore et al. |
| 5,187,102 A | 2/1993 | Stocker et al. |
| 5,189,019 A | 2/1993 | Palladino et al. |
| 5,194,589 A | 3/1993 | Bott |
| 5,196,403 A | 3/1993 | Maraganore et al. |
| 5,227,469 A | 7/1993 | Lazarus et al. |
| 5,238,919 A | 8/1993 | Zimmerman et al. |
| 5,239,058 A | 8/1993 | Vlasuk et al. |
| 5,246,715 A | 9/1993 | Orevi et al. |
| 5,256,559 A | 10/1993 | Maraganore et al. |
| 5,279,824 A | 1/1994 | Sawyer et al. |
| 5,321,010 A | 6/1994 | Connolly et al. |
| 5,324,715 A | 6/1994 | Connolly et al. |
| 5,328,997 A | 7/1994 | Vlasuk et al. |
| 5,340,726 A | 8/1994 | Connolly et al. |
| 5,367,056 A | 11/1994 | Hession et al. |
| 5,397,694 A | 3/1995 | Atkinson et al. |
| 5,455,181 A | 10/1995 | Strube et al. |
| 5,495,000 A | 2/1996 | Krstenansky |
| 5,523,287 A | 6/1996 | Friedrich et al. |
| 5,583,111 A | 12/1996 | Hemberger et al. |
| 5,587,360 A | 12/1996 | Sawyer |
| 5,705,355 A | 1/1998 | Tolstoshev et al. |
| 5,710,131 A | 1/1998 | Hemberger et al. |
| 5,723,312 A | 3/1998 | Noeske-Jungblut et al. |
| 5,731,288 A | 3/1998 | Markland, Jr. et al. |
| 5,756,454 A | 5/1998 | Noeske-Jungblut et al. |
| 5,780,303 A | 7/1998 | Pierschbacher et al. |
| 5,814,609 A | 9/1998 | Markland et al. |
| 5,824,505 A | 10/1998 | Tolstoshev et al. |
| 5,882,887 A | 3/1999 | Noeske-Jungblut et al. |
| 5,900,476 A | 5/1999 | Ruggeri et al. |
| 5,977,056 A | 11/1999 | Powell-Jones et al. |
| 6,025,330 A | 2/2000 | Sawyer et al. |
| 6,096,369 A | 8/2000 | Anders et al. |
| 6,186,974 B1 | 2/2001 | Allan et al. |
| 6,252,043 B1 | 6/2001 | Hession et al. |
| 6,277,824 B1 | 8/2001 | Doherty et al. |
| 6,291,205 B1 | 9/2001 | Tuite et al. |
| 6,307,025 B1 | 10/2001 | Hession et al. |
| 6,326,352 B1 | 12/2001 | Blaschuk et al. |
| 6,472,368 B1 | 10/2002 | Doherty et al. |
| 6,521,594 B1 | 2/2003 | Pierschbacher et al. |
| 6,589,992 B2 | 7/2003 | Uckun |
| 6,610,821 B1 | 8/2003 | Blaschuk et al. |
| 6,673,883 B1 | 1/2004 | Rowan |
| 6,710,030 B1 | 3/2004 | Markland et al. |
| 6,774,107 B1 * | 8/2004 | Strittmatter et al. ........... 514/12 |

(Continued)

FOREIGN PATENT DOCUMENTS

| | | |
|---|---|---|
| EP | 0 158 564 B1 | 10/1985 |
| EP | 0 255 206 A2 | 2/1988 |
| EP | 0 263 608 A2 | 4/1988 |
| EP | 0 263 608 A3 | 5/1989 |
| EP | 0 333 356 A2 | 9/1989 |

(Continued)

OTHER PUBLICATIONS

Kvist et al. (Vascular changes in the ruptured Achilles tendon and paratenon, International Orthopeadics, Springer Berlin/Heidelberg, vol. 16, No. 4, 1992, printed pp. 377-382, Printed pp. 1-6.*
Arefieva et al., "MCP-1-stimulated chemotxis of monocytic and endothelial cells is dependent on activation of different signaling cascades," Cytokine 31 (2005) 439-446.
Smith T. P. et al., "Saratin, an inhibitor of collagen-platelet interaction, decreases venous anastomotic intimal hyperplasia in a canine dialysis access model," Vasc. Endovasc. Surg. 37:259-269, 2003.
Vilahur, G. et al., "Antithromobotic effects of saratin on human atherosclerotic plaques," Thromb. Haemost. 2004; 92:191-200.
Case No. T0609/02 Decision on Appeal dated Oct. 27, 2004 for EP91917435.9.
Supplemental EP Search Report 06815841.9 received Oct. 26, 2009.

*Primary Examiner*—Sreeni Padmanabhan
*Assistant Examiner*—Timothy E Betton
(74) *Attorney, Agent, or Firm*—Wilson Sonsini Goodrich & Rosati

(57) ABSTRACT

The present invention provides compositions of saratin and methods of use thereof. One aspect of the invention is a method of prevention or mitigation of the development of adhesions, keloids and scars. The adhesions, keloids and scars can be due to surgery, such as plastic surgery or orthopedic surgery, or can be pre-existing scars. Another aspect of the invention is a method for treatment of flexor tendon injuries.

3 Claims, 9 Drawing Sheets

U.S. PATENT DOCUMENTS

| | | | |
|---|---|---|---|
| 6,780,845 B2 | 8/2004 | Blaschuk et al. | |
| 6,806,255 B2 | 10/2004 | Doherty et al. | |
| 6,881,722 B2 * | 4/2005 | Barnes et al. | ................. 514/12 |
| 6,906,707 B2 | 6/2005 | Takagi | |
| 2001/0007083 A1 | 7/2001 | Roorda | |
| 2002/0151475 A1 | 10/2002 | Blaschuk et al. | |
| 2002/0169207 A1 | 11/2002 | Uckun | |
| 2003/0060783 A1 | 3/2003 | Koole et al. | |
| 2003/0065136 A1 | 4/2003 | Blaschuk et al. | |
| 2003/0087811 A1 | 5/2003 | Blaschuk et al. | |
| 2003/0109454 A1 | 6/2003 | Doherty et al. | |
| 2003/0153731 A1 | 8/2003 | Hession et al. | |
| 2003/0161938 A1 | 8/2003 | Johnson | |
| 2003/0190342 A1 | 10/2003 | Barnes et al. | |
| 2003/0224978 A1 | 12/2003 | Blaschuk et al. | |
| 2004/0006011 A1 | 1/2004 | Gour et al. | |
| 2004/0106545 A1 | 6/2004 | Blaschuk et al. | |
| 2004/0132659 A1 | 7/2004 | Markland, Jr. et al. | |
| 2005/0143305 A1 | 6/2005 | Barnes et al. | |

FOREIGN PATENT DOCUMENTS

| | | |
|---|---|---|
| EP | 0 255 206 A3 | 11/1989 |
| EP | 0 348 208 A2 | 12/1989 |
| EP | 0 348 208 A3 | 5/1990 |
| EP | 0 372 670 A2 | 6/1990 |
| EP | 0 333 356 A3 | 12/1990 |
| EP | 0 419 099 A1 | 3/1991 |
| EP | 0 372 670 A3 | 8/1991 |
| EP | 0 442 843 A1 | 8/1991 |
| EP | 0 454 372 A1 | 10/1991 |
| EP | 0 468 764 A1 | 1/1992 |
| EP | 0 480 651 A1 | 4/1992 |
| EP | 0 487 238 A2 | 5/1992 |
| EP | 0 487 238 A3 | 6/1992 |
| EP | 0 530 937 B1 | 3/1993 |
| EP | 0 546 813 A2 | 6/1993 |
| EP | 0 552 269 B1 | 7/1993 |
| EP | 0 546 813 A3 | 1/1994 |
| EP | 0 887 369 A2 | 12/1998 |
| EP | 0 887 369 A3 | 12/1999 |
| EP | 1 132 406 A1 | 9/2001 |
| EP | 1311284 B1 | 12/2004 |
| WO | WO 85/04418 A1 | 10/1985 |
| WO | WO 86/03493 A1 | 6/1986 |
| WO | WO 87/00860 A1 | 2/1987 |
| WO | WO 89/09615 A1 | 10/1989 |
| WO | WO 90/06128 A1 | 6/1990 |
| WO | WO 90/08772 A1 | 8/1990 |
| WO | WO 90/12808 A1 | 11/1990 |
| WO | WO 90/13300 A1 | 11/1990 |
| WO | WO 91/12270 A2 | 8/1991 |
| WO | WO 91/12270 A3 | 9/1991 |
| WO | WO 91/15515 A1 | 10/1991 |
| WO | WO 91/15576 A1 | 10/1991 |
| WO | WO 92/01710 A1 | 2/1992 |
| WO | WO 92/07005 A1 | 4/1992 |
| WO | WO 92/11896 A1 | 7/1992 |
| WO | WO 93/01221 A1 | 1/1993 |
| WO | WO 93/05150 A1 | 3/1993 |
| WO | WO 93/09232 A1 | 5/1993 |
| WO | WO 93/11239 A1 | 6/1993 |
| WO | WO 93/16709 A1 | 9/1993 |
| WO | WO 93/17099 A1 | 9/1993 |
| WO | WO 93/25676 A1 | 12/1993 |
| WO | WO 94/26777 A1 | 11/1994 |
| WO | WO 95/00544 A1 | 1/1995 |
| WO | WO 95/01375 A1 | 1/1995 |
| WO | WO 96/08563 A1 | 3/1996 |
| WO | WO 96/34890 A2 | 11/1996 |
| WO | WO 96/34890 A3 | 10/1997 |
| WO | WO 98/02452 A2 | 1/1998 |
| WO | WO 98/02452 A3 | 3/1998 |
| WO | WO 98/11828 A1 | 3/1998 |
| WO | WO 98/30181 A1 | 7/1998 |
| WO | WO 98/30615 A1 | 7/1998 |
| WO | WO 99/02551 A1 | 1/1999 |
| WO | WO 99/33875 A1 | 7/1999 |
| WO | WO 00/02917 A2 | 1/2000 |
| WO | WO 00/02917 A3 | 5/2000 |
| WO | WO 00/31140 A1 | 6/2000 |
| WO | WO 00/56885 A1 | 9/2000 |
| WO | WO 00/58341 A1 | 10/2000 |
| WO | WO 01/39811 A1 | 6/2001 |
| WO | WO 01/41754 A2 | 6/2001 |
| WO | WO 01/41754 A3 | 6/2001 |
| WO | WO 01/47572 A2 | 7/2001 |
| WO | WO 01/77146 A2 | 10/2001 |
| WO | WO 01/77146 A3 | 10/2001 |
| WO | WO 02/15919 A2 | 2/2002 |
| WO | WO 02/15919 A3 | 5/2002 |
| WO | WO 03/072154 A1 | 9/2003 |

* cited by examiner

A

B. 10 μg/mL Collagen

C. 10 μg/mL BSA

A. 1 mg/mL Collagen

B. 1 mg/mL BSA

C. 1 mg/mL Fibronectin

FIGURE 7
SEQUENCE LISTINGS

FIG 7A

SEQ ID NO 1
LENGTH: 375
TYPE: DNA
ORGANISM: Hirudo medicinalis
LOCATION: (64)..(372)
SEQUENCE: 1

```
    atgaagtatt tcttgatttc cttcctttgc ctcgcaagct tgctgatctc aactacttct        60
    tca gaa gaa cgt gaa gat tgt tgg acg ttt tac gcg aac aga aaa tat         108
        Glu Glu Arg Glu Asp Cys Trp Thr Phe Tyr Ala Asn Arg Lys Tyr
        1               5                   10                  15
    aca gac ttc gat aaa tct ttt aag aag tcc tct gat ctt gac gaa tgc         156
    Thr Asp Phe Asp Lys Ser Phe Lys Lys Ser Ser Asp Leu Asp Glu Cys
                    20                  25                  30
    aaa aaa aca tgt ttc aag acg gag tac tgc tac atc gtt ttt gaa gac         204
    Lys Lys Thr Cys Phe Lys Thr Glu Tyr Cys Tyr Ile Val Phe Glu Asp
                35                  40                  45
    acg gtc aac aag gaa tgt tac tac aat gtc gtt gat ggt gaa gag tta         252
    Thr Val Asn Lys Glu Cys Tyr Tyr Asn Val Val Asp Gly Glu Glu Leu
            50                  55                  60
    gac caa gaa aaa ttt gtt gtc gac gaa aac ttc acg gaa aat tat ttg         300
    Asp Gln Glu Lys Phe Val Val Asp Glu Asn Phe Thr Glu Asn Tyr Leu
        65                  70                  75
    aca gac tgc gag ggt aaa gat gca ggt aat gcg gca ggt aca ggt gac         348
    Thr Asp Cys Glu Gly Lys Asp Ala Gly Asn Ala Ala Gly Thr Gly Asp
    80                  85                  90                  95
    gag tca gat gaa gtt gat gaa gat taa                                     375
    Glu Ser Asp Glu Val Asp Glu Asp
                        100
```

SEQ ID NO 2
LENGTH: 103
TYPE: PRT
ORGANISM: Hirudo medicinalis
SEQUENCE: 2

```
    Glu Glu Arg Glu Asp Cys Trp Thr Phe Tyr Ala Asn Arg Lys Tyr Thr
    1               5                   10                  15
    Asp Phe Asp Lys Ser Phe Lys Lys Ser Ser Asp Leu Asp Glu Cys Lys
                    20                  25                  30
    Lys Thr Cys Phe Lys Thr Glu Tyr Cys Tyr Ile Val Phe Glu Asp Thr
                35                  40                  45
    Val Asn Lys Glu Cys Tyr Tyr Asn Val Val Asp Gly Glu Glu Leu Asp
            50                  55                  60
    Gln Glu Lys Phe Val Val Asp Glu Asn Phe Thr Glu Asn Tyr Leu Thr
        65                  70                  75                  80
    Asp Cys Glu Gly Lys Asp Ala Gly Asn Ala Ala Gly Thr Gly Asp Glu
                        85                  90                  95
    Ser Asp Glu Val Asp Glu Asp
                        100
```

FIGURE 7B

SEQ ID NO 3
LENGTH: 23
TYPE: DNA
ORGANISM: Artificial Sequence
FEATURE:
OTHER INFORMATION: r = a or g; m = a or c; y = c or t; and n =a
    or g or c or t
OTHER INFORMATION: Description of Artificial Sequenceprimer01
SEQUENCE: 3
    gargarmgng argaytgttg gac                                   23

SEQ ID NO 4
LENGTH: 23
TYPE: DNA
ORGANISM: Artificial Sequence
OTHER INFORMATION: r = a or g; m = a or c; y = c or t; and n = a
    or g or c or t
OTHER INFORMATION: Description of Artificial Sequenceprimer02
SEQUENCE: 4
    gargarmgng argaytgctg gac                                   23

SEQ ID NO 5
LENGTH: 24
TYPE: DNA
ORGANISM: Artificial Sequence
OTHER INFORMATION: Description of Artificial Sequenceprimer03
SEQUENCE: 5
    gcatcgatgg aagaacgtga agac                                  24

SEQ ID NO 6
LENGTH: 23
TYPE: DNA
ORGANISM: Artificial Sequence
OTHER INFORMATION: Description of Artificial Sequenceprimer04
SEQUENCE: 6
    tagcgctttt gacgtcgtcg tca                                   23

SEQ ID NO 7
LENGTH: 26
TYPE: DNA
ORGANISM: Artificial Sequence
OTHER INFORMATION: Description of Artificial Sequenceprimer05
SEQUENCE: 7
    gaagaatgca aggatgagga ttattg                                26

SEQ ID NO 8
LENGTH: 25
TYPE: DNA
ORGANISM: Artificial Sequence
OTHER INFORMATION: Description of Artificial Sequenceprimer06
SEQUENCE: 8
    aagcttctag tcttcgtcaa cttcg                                 25

FIGURE 7C

SEQ ID NO 9
LENGTH: 94
TYPE: DNA
ORGANISM: Artificial Sequence
OTHER INFORMATION: Description of Artificial Sequenceprimer07
SEQUENCE: 9
```
    cggatccatg aaattcttag tcaacgttgc ccttgttttt atggtcgtat acatttctta    60
    catctatgcg gaagaacgtg aagattgttg gact                                94
```

SEQ ID NO 10
LENGTH: 24
TYPE: DNA
ORGANISM: Artificial Sequence
OTHER INFORMATION: Description of Artificial Sequenceprimer08
SEQUENCE: 10
```
    ggtacctcac atatcttcat caac                                           24
```

SEQ ID NO 11
LENGTH: 30
TYPE: DNA
ORGANISM: Artificial Sequence
OTHER INFORMATION: Description of Artificial Sequenceprimer09
SEQUENCE: 11
```
    gcatgcggcc gcctaatctt catcaacttc                                     30
```

SEQ ID NO 12
LENGTH: 27
TYPE: DNA
ORGANISM: Artificial Sequence
OTHER INFORMATION: Description of Artificial Sequenceprimer10
SEQUENCE: 12
```
    gcatgaattc gaagaacgtg aagattg                                        27
```

METHODS AND COMPOSITIONS FOR BLOCKING PLATELET AND CELL ADHESION, CELL MIGRATION AND INFLAMMATION

CROSS-REFERENCE

This application is related to and claims priority to U.S. Provisional Application No. 60/721,754, filed Sep. 28, 2005, which is incorporated herein by reference in its entirety.

BACKGROUND OF THE INVENTION

The response to injury is an innate host immune response for restoration of tissue integrity. Wound healing, whether initiated by trauma, surgery, microbes or foreign materials, proceeds via an overlapping pattern of events including coagulation, inflammation, epithelialization, formation of granulation tissue, matrix and tissue remodeling. The process of repair is mediated in large part by interacting molecular signals, including cytokines that motivate and orchestrate the manifold cellular activities which underscore inflammation and healing.

The initial injury triggers coagulation and an acute local inflammatory response followed by mesenchymal cell recruitment, proliferation and matrix synthesis. Failure to resolve the inflammation can lead to chronic non-healing wounds, whereas uncontrolled matrix accumulation, often involving aberrant cytokine pathways, leads to excess scarring and fibrotic sequelae.

Most types of injury damage blood vessels, and coagulation is a response to initiate hemostasis and protect the host from excessive blood loss. Vessel wall injury exposes collagen to elements of flowing blood. Collagen is a thrombogenic surface component and has been shown to be a stimulant for platelet adhesion, aggregation and the release of their granules leading to the recruitment of (Ruggeri, Z. M. et al.; Seminars in Hematology, 1994, 31, 229-39) additional platelets to this area to form aggregates or a thrombus. The initial contact of the platelets to the vessel surface is mediated by collagen bound von Willebrand Factor (vWF) and a specific vWF receptors on platelets, the glycoprotein Ib-V-IX complex. This reversible adhesion allows platelets to roll over the damaged area, which is then followed by a firm adhesion mediated by the collagen receptors (alpha(2)beta(1), GPVI) in addition resulting in platelet activation. This leads to the conformational activation of the platelet alpha(IIb)beta3 receptor, fibrinogen binding and finally to platelet aggregation. In addition ADP, epinephrine and circulating clotting factors drive the further activation process of platelets while simultaneously an increase in thrombin activity contributes to the formation of the cross-linked fibrin clot. Platelet-platelet aggregation supports this process and is driven by fibrinogen as a mediator that bridges cells through the glycoprotein IIb/IIIa receptor.

This normal physiological response plays a role in the course of pathological processes where platelets adhere to collagen exposed in sclerotic lesions (Van der Rest M. et al.; FASEB Journal, 1991, 5, 2814-23) and start to build-up occlusions. Depending on the location and extent of the occlusion complications such as myocardial infarction, stroke, inflammation or pulmonary embolism may be the outcome of this process.

As a direct acting antithrombotic agent heparin which blocks the thrombin activity, thus preventing the formation of fibrin rich thrombi, is currently used in anti-thrombotic interventions. Heparin is used in indications such as: unstable angina and acute myocardial infarction. However, several short comings of heparin such as intravenous application, requirement for anti-thrombin-III as a cofactor, reduced affinity for clot-bound thrombin, it's inactivation by several plasma proteins, the occasional induction of thrombocytopenia and it's biological heterogeneity remain unresolved.

Recent development of low molecular weight heparin has contributed a version for subcutaneous application; however the therapeutic benefit over the standard heparin has been modest. Unfortunately, the same applies to the other directly acting antithrombins such as hirudin, hirulog and warfarin. One of the problems seems to be related to the increased production of thrombin under antithrombotic treatment (Rao, A. K et al., Circulation, 1996, 94, 389-2395).

Other recent strategies have therefore been focused to the process of prothrombin activation which is driven by Factor Xa. The challenge is the design of appropriate inhibitors directed to this factor.

Another panel of therapeutics is represented by the thrombolytic regimens and has been focused on the development of staphylokinase, streptokinase, urokinase type plasminogen activator, tissue type plasminogen activator and anisoylated-plasminogen-streptokinase activator complex. The differences in time necessary to inducing reperfusion is different for each of these thrombolytic agents, however the contribution in terms of reducing the overall mortality is equal for all the products. In addition, reocclusion and/or prolonged bleeding are some of the complications. This might be due to relatively low specificity for fibrin and the short plasma half-life of these compounds.

A complication arises when artificial surfaces come in contact with blood. When this is the case, there is increased tendency to induce thrombotic events by activation of platelets and/or induction of coagulation. These effects may cause failure of vascular grafts, cardiac valves; stents, catheters or any other blood contacting device or material. The protein disclosed herein has the ability to create non-thrombogenic surfaces and can therefore be further exploited by immobilization of this protein to the materials and devices described above. Such a treatment renders such materials or devices biocompatible and thromboresistant.

The two lines of therapy, which are currently being used in an attempt to control platelet adhesion, activation and subsequent thrombosis and intimal hyperplasia, are anti-platelet agents and anti-thrombotic administration. Although drugs such as aspirin effectively block the synthesis of Thromboxane A2 through inhibition of the cyclooxygenase pathway, they do not prevent the collagen-induced platelet adhesion and activation, which stimulate the development of intimal hyperplasia. The use of heparin as an antithrombotic agent is associated with complications and limitations including a non-predictable dose response, need for close laboratory monitoring, limited activity against clot bound thrombin, multiple inhibitory sites, antithrombin III dependency, a risk of bleeding, as well as a need for continuous infusion. Clearly, an ideal therapeutic agent would be one that produces site specific and localized effects without systemic distribution or a generalized coagulopathy.

Due to the limitations associated with the available antithrombotic agents there is an actual need for new alternative strategies and therapeutics. Therefore, the need for new and improved therapeutics and methods for inhibiting the events in the pathophysiology of platelet adhesion is obvious, and contributions in this field are expected to decrease morbidity and mortality associated with angioplasitic or surgical procedures.

INCORPORATION BY REFERENCE

All publications and patent applications mentioned in this specification are herein incorporated by reference to the same extent as if each individual publication or patent application was specifically and individually indicated to be incorporated by reference.

SUMMARY OF THE INVENTION

A first aspect of the present invention relates to methods for treating white blood cell mediated inflammatory conditions by administering to a patient in need thereof an effective amount of saratin. In one embodiment, saratin inhibits adhesion or cell migration of white blood cells such as lymphocytes, monocytes, macrophages or polymorphonuclear leukocytes. In yet another embodiment, the saratin is used for the treatment of platelet-mediated inflammation.

Another aspect of the invention is directed to methods for inhibiting cell migration and/or cell adhesion to extracellular matrix proteins. In one embodiment, saratin prevents cell adhesion to extracellular matrix proteins of inflammatory cells. In another embodiment, the extracellular matrix protein is collagen, albumin, elastin or fibronectin.

In addition, the invention is directed to methods for treating surgically-induced complications with saratin. The surgically-induced complications are typically associated with surgically-induced inflammation. In one embodiment, an effective amount of saratin is administered to a patient in order to treat surgically-induced inflammation. Surgically-induced complications may also be surgically-induced adhesions. In another embodiment, an effective amount of saratin is administered to a patient in order to treat surgically-induced adhesions. In one embodiment, saratin prevents surgically-induced adhesion of platelets and/or white blood cells. In one embodiment, saratin prevents surgically-induced adhesion of lymphocytes, monocytes, macrophages or polymorphonuclear leukocytes. In one embodiment, saratin is used for the treatment of surgery-induced complications induced by an orthopedic or plastic surgery. In one embodiment, saratin is used for the inhibition of cell migration to a site of injury, such as injury caused by surgery.

The effective amount of saratin may be administered as a topical agent or a coating for an implant. The implant may be a natural or artificial implant. The artificial implant may be a medical device such as a plastic surgery implant, a cardiovascular implant or an orthopedic implant. In one embodiment, the medical device is a cardiac valve, a graft, a stent, a catheter, a spinal disc, a rod, a screw, a plate, a cartilage, or an adhesion barrier. The natural implant may be an organ, a tissue, a tissue graft, or a cellular implant. In one embodiment, the natural implant is a vascular graft. Preferably, saratin is applied as a topical agent at the site of surgery.

In one embodiment, saratin is used to coat a graft, a transplant, or a device prior to implantation. In another embodiment, saratin is applied to the graft, transplant, or device post-implantation. In another embodiment, saratin is applied on the site of surgical injury. In yet another embodiment, saratin is applied to injured tissue to prevent scarring during the healing process. The injury to the tissue could be due to surgery, burn, or an inflammatory condition.

In yet another aspect of the invention, saratin is used to prevent and/or treat scar and keloid formations. The scar and/or keloids may be surgically-induced or due to burn or inflammatory skin disease. In one embodiment, the scar and/or keloids are due to plastic surgery. In one embodiment, saratin is administered to inhibit scar tissue resulting from a surgical procedure such as a knee, shoulder or hip arthrotomy or implantation of an orthopedic device, in particular by surgical implant such as a knee, hip, or shoulder replacement or other implanted article. In another embodiment of the invention, saratin is directly injected into a wrinkle of a patient who has had cosmetic alteration of the wrinkle to prevent scar tissue formation.

DESCRIPTION OF THE DRAWINGS

A better understanding of the features and advantages of the methods and compositions that are described herein may be obtained by reference to the following detailed description that sets forth illustrative embodiments, and the accompanying drawings of which:

FIG. 7 depicts the sequence listings.

DETAILED DESCRIPTION OF THE INVENTION

Definitions and General Parameters

Figure 1:
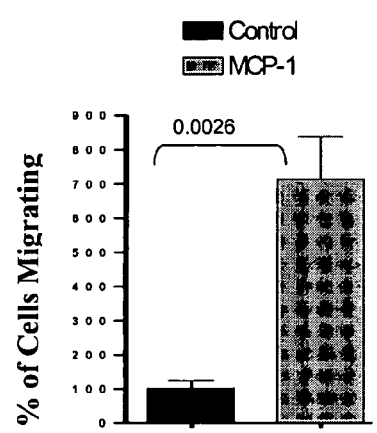
FIG. 1 depicts the effect of saratin on MCP-1-induced human monocyte migration in 10 µg/mL collagen Type IV and BSA coated filters.
Figure 1:
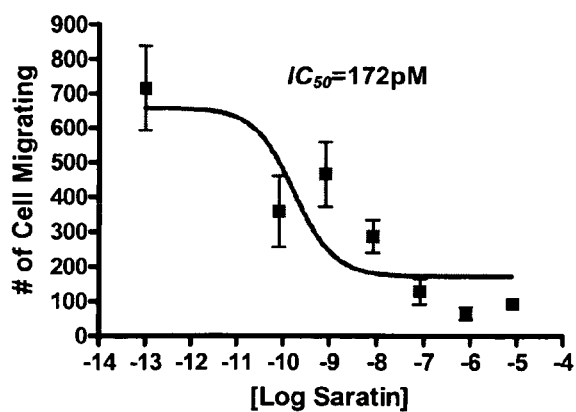
Figure 1:
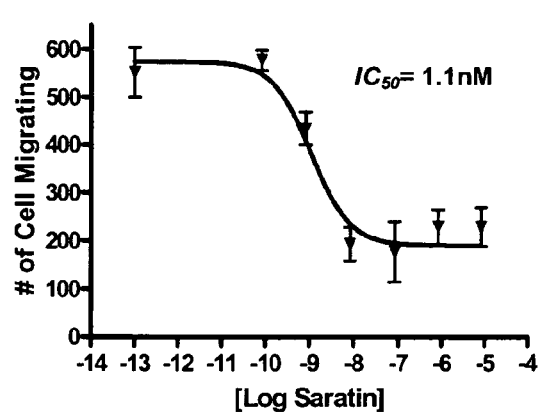
Figure 2:
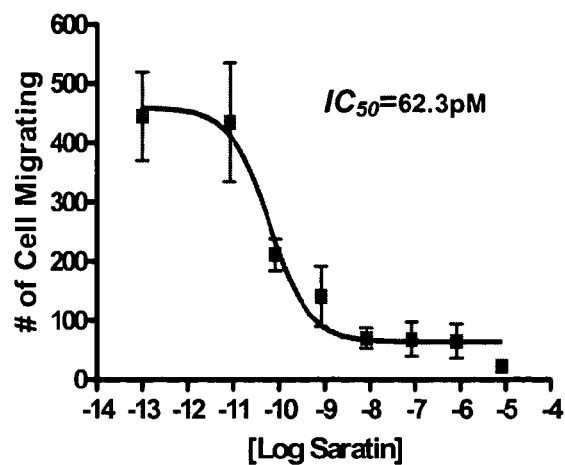
FIG. 2 depicts the effect of saratin on MCP-1-induced human monocyte migration in 1 mg/mL BSA, 1 mg/mL collagen, or 1 mg/mL fibronectin coated filters.
Figure 2:
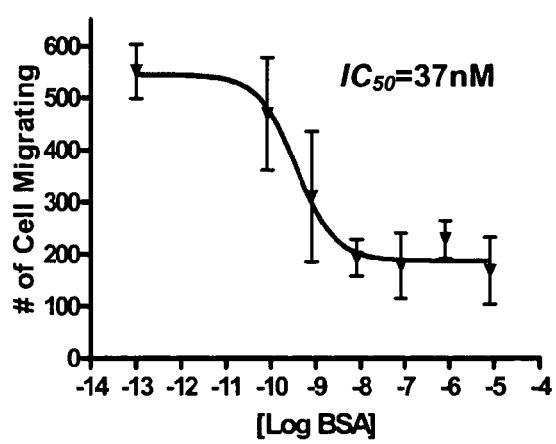
Figure 2:
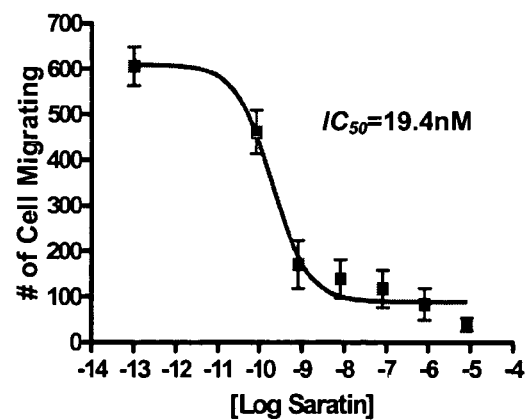
Figure 3:
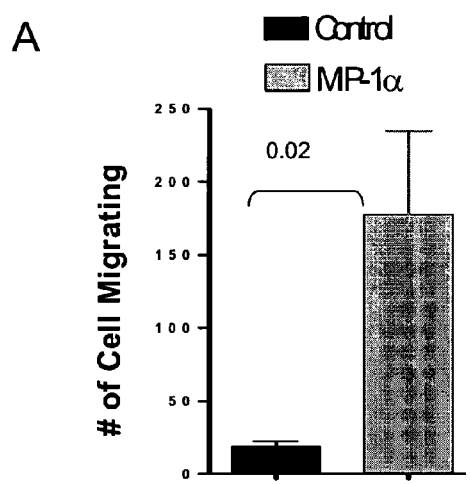
FIG. 3 depicts the effect of saratin on MIP-1α-induced human T lymphocyte migration in 10 µg/mL collagen Type IV and BSA coated filters.
Figure 3:
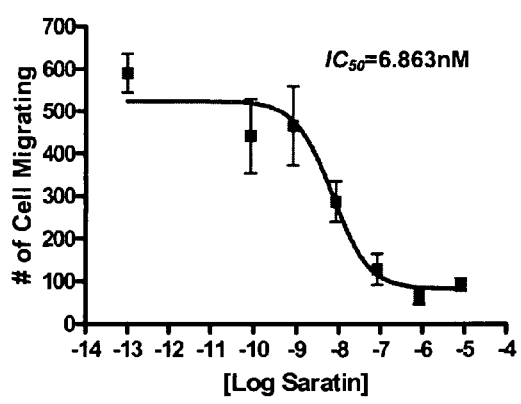
Figure 3:
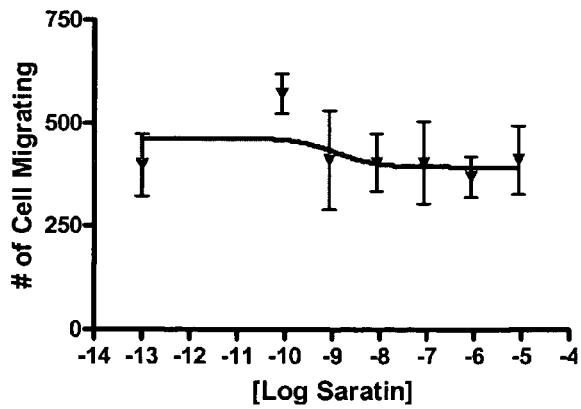
Figure 4:
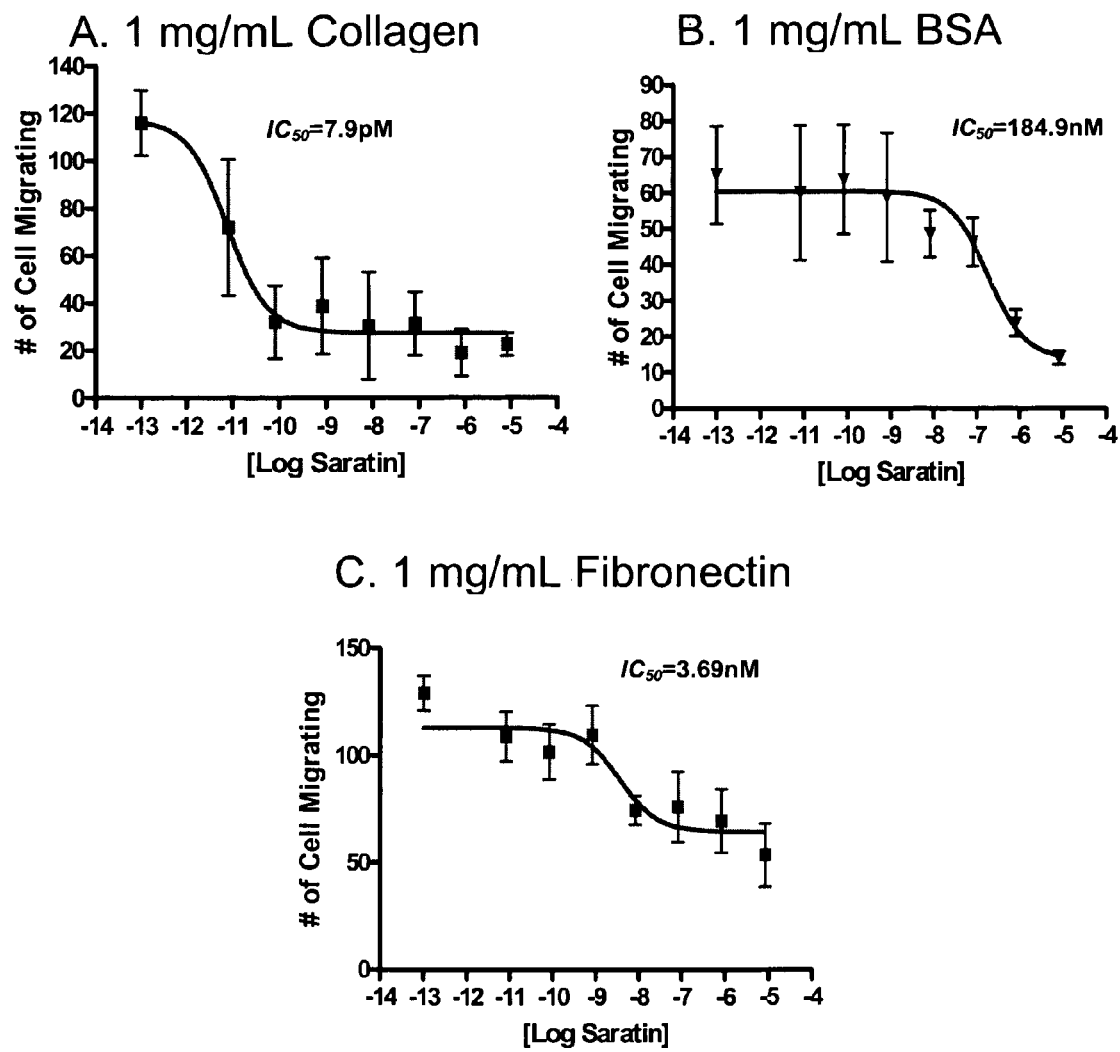
FIG. 4 depicts the effect of saratin on MIP-1α-induced human T lymphocyte migration in 1 mg/mL BSA, 1 mg/mL collagen Type IV, or 1 mg/mL fibronectin coated filters.

As used in the present specification, the following words and phrases are generally intended to have the meanings as set forth below, except to the extent that the context in which they are used indicates otherwise.

The term "effective amount" or "therapeutically effective amount" refers to that amount of saratin that is sufficient to effect treatment, as defined below, when administered to an animal subject in need of such treatment. The therapeutically effective amount will vary depending upon the subject and disease condition being treated, the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular saratin compounds chosen, the dosing regimen to be followed, whether it is administered in combination with other compounds, timing of administration, the tissue to which it is administered, and the physical delivery system in which it is carried.

The term "treating" and its grammatical equivalents as used herein includes achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "therapeutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Saratin

Saratin is a naturally occurring protein isolated from the saliva of the medicinal leech *Hirudo medicinalis*, described in U.S. Pat. Nos. 6,774,107 and 6,881,722. Saratin has been shown to bind to collagen thus acting as an inhibitor of natural platelet adhesion to collagen. Specifically, it has been shown that saratin blocks vWF binding to collagen and effectively prevents the adhesion of platelets to collagen under elevated shear. Furthermore, as described in the studies herein saratin inhibits chemokine-induced migration.

Saratin was sequenced and the gene was cloned from a *H. medicinalis* cDNA-library. Saratin is characterized by the amino acid sequences depicted in the sequence of SEQ. ID. NO. 2 and is constituted of 103 amino acids which make up a theoretical relative molecular weight of approximately 12068 dalton±1 kDa. The protein exhibits a unique primary structure with no similarity to other previously described sequences. Saratin is rich in aspartic and glutamic acid which contribute to the acidic isoelectric point of pH 3.7.+−.0.5 of the molecule as measured by IEF-PAGE. SDS-PAGE analysis demonstrated a shift in mobility upon reduction of the protein prior to electrophoresis, indicating post-translational modifications. Sequencing of the polypeptide had revealed six cysteine molecules which could make-up post-translational modifications of the protein. Electrospray mass spectrometry of saratin revealed an actual molecular weight of 12061 dalton indicating that up to three disulphide bonds are involved in the formation of the secondary structure of the native form of the protein.

Saratin can be produced by procedures such as recombinant techniques. Suitable recombinant saratin for use in the invention was expressed and isolated from *Hansenula polymorpha*. The recombinant and the naturally occurring proteins are potent inhibitors of collagen-dependent platelet adhesion and as shown herein a non-specific inhibitor of matrix proteins needed for cellular migration, and therefore can be useful for the therapeutic treatment of various conditions related to heart disease, diseases of the circulation system, and inflammatory conditions. Furthermore, saratin is useful for coating natural or artificial collagen surfaces in order to render them nonadhesive for cells and prevent the activation of cells.

In general, the present invention involves the introduction of saratin into or onto a selected location within or on a lumen in a tissue, e.g., the vasculature or an organ, under conditions such that saratin may be used locally as a topical agent or as an adherent coating on the surface to prevent and inhibit an undesirable thrombotic response to tissue injury or undesirable cell migration, including injury associated with surgery, burns, tissue transplants or autoimmune diseases. Saratin can be combined with a variety of therapeutic agents for on-site delivery.

It has been pointed out earlier that various therapeutic interventions induce local-injuries which would ideally be treated immediately and locally. Left untreated the injured cells initiate a series of processes involved in clotting, complement activation, and cellular response to release of cytokines, induction of proliferation, and other biologically active processes. In some embodiments of the present invention it is therefore an aspect that saratin is located directly in the manipulated tissues. Another aspect of the local application is the minimization of potential problems related to the systemic effects of the agents used for intervention.

The present invention comprises formulations and methods of use of the active polypeptide saratin isolated from the leech *Hirudo medicinalis*. The protein can be isolated from saliva by a combination of pressurized dialysis and at least one chromatographic step like hydrophobic interaction chromatography (HIC) and/or at least one anionic exchange chromatography and optionally at least one reverse phase high performance chromatography (RP-HPLC) step.

The present invention as well relates to isolated DNA comprising a polynucleotide encoding the leech derived platelet adhesion inhibitor having the amino acid sequence as shown for the protein. The nucleotide sequence representing the cDNA clone is shown in SEQ. ID. NO. 1. Position 1-63 of the nucleotide sequence represents a putative 21 amino acid leader sequence and position 64-372 contains an open reading frame coding for a polypeptide of 103 amino acid residues and an amino acid sequence as shown for the mature protein in SEQ. ID. NO. 2. SEQ. ID. NO. 1 and 2 are depicted in FIG. 7A. FIGS. 7B and 7C depict SEQ. ID. NO. 3-12. The SEQ. ID. NO. 3-12 are sequence of primers that were used in amplification and isolation of the saratin gene by PCR, construction of *E. Coli* expression vector and expression, construction of the baculo donor plasmid and expression, and yeast expression vector and expression, as described in U.S. Pat. No. 6,774,107, which is hereby incorporated by reference in its entirety.

The present invention also relates to recombinant vectors which include the synthetic gene coding for the leech-derived platelet adhesion inhibitor of the present invention, and a host cell containing the recombinant vectors. Methods for recovering and isolating the expressed proteins are based on tag-technologies or are adapted from the purification scheme developed for the naturally occurring saratin. Depending on the individual protocols used for extracellular or intracellular expression in yeast cells, insect cells, baby hamster kidney cells and *E. coli* cells transformed with the appropriate vectors the steps for recovering the recombinant protein from the supernatant or sediments can be suitably adapted by techniques known to a person of skill in the art. Suitable expression was found in *E. coli* as a host, where periplasmatic expression was contributed by insertion of a pelB leader sequence. Products recovery from *Escherichia coli* (*E. coli*) was achieved (around 5 mg/L) after osmolysis and centrifugation. *Saccharomyces cerevisiae* (*S. cerevisiae*) (>10 mg/L culture broth) with the alterative yeast adopted vector was used in a paralleled experiment. The secreted material was isolated by centrifugation. Purification was achieved by cross-flow filtration and ion exchange chromatography. In other expression approaches using either COS cells or CHO cells, product expression was approximately about 750 ng/mL. The purified recombinant material proved to be pure and homogeneous by electrophoretic and chromatographic analysis and identical to saliva derived saratin as demonstrated by amino acid sequencing and molecular mass determination. Techniques for the production of saratin are disclosed in U.S. Pat. No. 6,774,107. For instance transgenic mice, or other organisms, including other mammals, may as well be used to express saratin.

The protein, saratin, of the present invention includes variants which conserve the activity of the disclosed sequences, including fragments or subunits, naturally occurring variants, allelic variants, randomly generated artificial mutants and intentional sequence variations such as adding amino acids which conserve activity, inverse peptide and peptides containing D-amino acids. Fragments or subunits refer to any portion of the sequence which contains fewer amino acids than the complete protein e.g. partial sequences excluding portions of the N- and/or C-termini of the complete protein. For example, the protein of the present invention includes a proteolytic fragment of saratin with molecular weight of 10 kDa observed during the isolation process by SDS PAGE analysis. The protein also includes modified forms with one or more non-natural amino acids or other modifications, such as pegylation or glycosylation. For example, the protein includes the glycosylated product from yeast.

The invention further covers hybrid proteins, such as fusion proteins or proteins resulting from the expression of multiple genes within the expression vector, and may include a polypeptide having the specific activity of a disclosed protein linked by peptide bonds to a second polypeptide. Notably other variants of the proteins of the present invention are included, especially any variants that differ from the isolated protein only by conservative amino acid substitution. Such conservative amino acid substitutions are defined, for example, in Taylor et al., J. Mol. Biol., 1986, 188, 233.

vWF-Dependent Binding of Platelets

The invention relates to the effect of a polypeptide called saratin that decreases platelet adhesion and accumulation after injuries. The invention furthermore relates to the inhibition of vWF-dependent binding of platelets to collagen and also medical uses of saratin as an inhibitor of thrombosis wherein said polypeptide is used locally as a topical agent or as a coating for implants such as biological implants (organs, cells or tissue) and medical devices.

The adhesion of blood cells especially platelets to the injured tissues, including blood vessels, is a known phenomenon in surgical procedures. Such injuries may occur during various surgical and percutaneous therapies that have been developed to reopen blocked channels, conduits, and other lumens, to remove diseased tissue, and to implant substitute tissue, medical devices or components thereof.

The cellular and molecular response of tissues to mechanically induced trauma, surgical intervention, stent placement, placement of a graft is an interaction of inflammation, smooth muscle cell migration, proliferation and myofibroblast transformation that occurs as soon as the trauma occurs (Futura; 1997. p. 289-317). Intervention may also cause some degree of additional injury with local de-endothelialisation and exposure of underlying extracellular matrix components such as collagen and elastin. In some patients the recruitment of platelets and fibrinogen can then result in an acute thrombotic occlusion.

The adherence of platelets to the injured blood vessel walls is mediated in the first instance by von Willebrand factor (vWF), a multimeric glycoprotein that is released from endothelial cells and circulates in the plasma, where it functions as a carrier protein for factor VIII (Annu. Rev. Biochem. 1998; 67:395-424). Highly multimerized vWF also circulates contained within alpha-granules of platelets, from where it is released following platelet activation (Annu. Rev. Biochem. 1998; 67:395-424). Under elevated shear conditions, such as those encountered in arteries at sites of atheromatous plaque or mechanical intervention, vWF may bind, via its A3 domain, to surface-exposed collagen fibers (Biochemistry 1986; 25(26):8357-8361, Blood 1987; 70(5):1577-1583, J. Biol. Chem. 1987; 262(28):13835-13841). COLLAGEN-bound vWF in turn then "tethers" platelets via shear-dependent exposure of an epitope in the vWF-A1 domain, which interacts with platelet GPIb/IX/V (Blood 1985; 65(1):85-90, Blood 1985; 65(4):823-831, Br. J. Haematol 1986; 63(4):681-691). Thus vWF acts as a bridge between collagen and platelets and is a prerequisite for the adhesion of platelets to collagen under flow (J. Lab. Clin. Med. 1974; 83(2):296-300). Platelet rolling over vWF results in weak adhesion, however, and additional, direct interactions between collagen and other receptors on the platelet surface are required in order to facilitate permanent platelet adhesion, activation and aggregation (Thromb. Haemost 1997; 78(1):434-438, Thromb. Haemost 1997; 78(1):439-444). Direct collagen receptors on platelets include GP VI (Blood 1987; 69(6):1712-1720, Thromb. Haemost 1999; 81(5):782-792, J. Clin. Invest. 1989; 84(5):1440-1445), GP Ia/IIa ($\alpha_2/\beta_1$) (J. Clin. Invest. 1989; 84(5):1440-1445, Nature 1985; 318(6045):470-472), and to a lesser extent GP IV (CD36) (J. Biol. Chem. 1989; 264(13):7576-7583) and perhaps even p65 (J. Clin. Invest. 1997; 100(3):514-521). In the absence of vWF-assisted platelet binding, these receptors have proven to be weak in mediating platelet recruitment to collagen under flow conditions (Br. J. Haematol 1986; 63(4):681-691). Finally vWF, in combination with fibrinogen, facilitates the cross-linking and further activation of platelets via binding to platelet GP IIb/IIIa (J. Clin. Invest. 2000; 105(6):783-791), providing stability and strength to the developing thrombus.

With the advent of platelet GP IIb/IIIa and ADP receptor antagonists strides forward in anti-aggregatory therapy have been made in recent years (Coronary Art Dis 1999; 10(8):553-560, J. Am. Coll. Surg. 2000; 191(1):76-92). However, these strategies are not designed to inhibit the initial adhesion of platelets to exposed collagen fibers, and despite the efficacy of GP IIb/IIIa antagonists in attenuating platelet-platelet interactions, platelets still adhere to the injured vessel wall (Blood 1993; 81(5):1263-1276, Circulation 1995; 91(5):1354-1362). Furthermore, platelet activation almost certainly extends beyond aggregation and acute thrombosis, the progression of sub-acute and chronic intimal hyperplasia being at least partially affected by mitogenic mediators such as platelet-derived growth factor (PDGF), released by the activation of platelets. Indeed, the inhibition of PDGF has been demonstrated to reduce intimal hyperplasia in various animal species (Science 1991; 253(5024):1129-1132, Circulation 1999; 99(25):3292-3299).

Several leech-derived substances have been reported to inhibit collagen-platelet interactions (Blood 1995; 85(3):705-711, Platelets 2000; 11(2):83-86, J. Biol. Chem. 1992; 267(10):6893-6898, J. Biol. Chem. 1992; 267(10):6899-6904, Blood Coagul Fibrinolysis 1991, 2(1):179-184). Destabilase, an isopeptidase with fibrin depolymerising activity isolated from *Hirudo medicinalis*, has been reported to inhibit platelet aggregation induced by various agonists, including collagen, but is believed to bind directly to the platelet membrane (Platelets 2000; 11(2):83-86). Leech antiplatelet protein (LAPP), a ~13 kDa protein from the saliva of *Haementeria officinalis*, inhibits platelet adhesion to collagen under static conditions (J. Biol. Chem. 1992; 267(10):6899-6904, Thromb. Haemost 1999, 82(3):1160-1163) and elevated flow (Arterioscler Thromb. Vasc. Biol. 1995, 15(9): 1424-1431), with effects on both vWF- and platelet GP Ia/IIa-mediated binding to collagen (Thromb. Haemost 1999, 82(3): 1160-1163). Calin is a ~65 kDa protein from *Hirudo medicinalis* for which a similar profile has emerged. Calin also inhibits collagen-platelet interactions under both static and flow conditions (Blood 1995; 85(3):705-711, Blood Coagul Fibrinolysis 1991, 2(1):179-184, Thromb. Haemost 1999, 82(3):1160-1163). Furthermore, both LAPP and Calin are inhibitors of collagen-induced platelet aggregation, inhibiting aggregation at concentrations similar to those which block vWF binding to collagen (J. Biol. Chem. 1992; 267 (10):6893-6898, Blood Coagul Fibrinolysis 1991, 2(1):179-184, Blood 1995, 85(3):712-719).

Inflammation

The invention also relates to the effect saratin on inflammation. The invention furthermore relates to the inhibition of cell migration and also medical uses of saratin as an inhibitor of inflammation wherein said polypeptide is used locally as a topical agent or as a coating for biological implants such as organs, cells or tissue and medical devices.

Inflammation is the first response of the immune system to infection or irritation and may be referred to as the innate cascade. Inflammation has two components: (i) cellular and (ii) exudative.

The exudative component involves the movement of fluid, usually containing many important proteins such as fibrin and immunoglobulins. Blood vessels are dilated upstream of an infection and constricted downstream while capillary permeability to the affected tissue is increased, resulting in a net loss of blood plasma into the tissue—giving rise to edema or swelling.

The cellular component involves the movement of white blood cells from blood vessels into the inflamed tissue. The white blood cells, or leukocytes, take on a role in inflammation; they extravasate from the capillaries into tissue, and act as phagocytes, picking up bacteria and cellular debris. For instance, without being limited to any theory, lymphocytes and monocytes recruited to the inflamed tissue and also macrophages release chemokines that further recruit polymorphonuclear leukocytes. White blood cells may also aid by walling off an infection and preventing its spread.

Cell migration occurs when the cells start to tether on the surface of the endothelium through L-selectin binding. Firm adhesion then takes place aided by the interaction of adhesion molecules such as LFA-1 present on the surface of the cells to their ligand molecules (e.g. VCAM and ICAM) present on endothelial cells. This process is strengthened by chemokines which regulate the affinity of this interaction. After this transmigration takes places, a step requires the imagination of the cells and their binding to extracellular matrix proteins (ECM). Eventually the cells start to migrate toward the concentration gradients of chemokines. Hence binding of cells to ECM plays a role in their migration toward inflammatory sites. In the studies described herein the ability of monocytes and T lymphocytes to migrate toward the concentration gradients of chemokines was examined. However, first the cells must bind to ECM prior to their migration Preferably, saratin is designed to be applied during surgery to the endovascular surface where it coats the exposed collagen and inhibits vWF-dependent and $\alpha_2\beta_1$ integrin binding of platelets to arterial wall collagens. In preventing platelet adhesion to damaged vessels, saratin blocks the first step in a sequence of events involving platelet aggregation and activation and may thereby prevents the subsequent thrombus formation and intimal hyperplasia that occurs in a range of vascular surgical and endovascular procedures. The specificity of saratin for collagen was a matter of investigation in the studies described herein. In addition, the efficacy of saratin on the in vivo accumulation of cells and the secretion of pro-inflammatory and inflammatory cytokines during inflammation was examined.

To this end, the filters used for chemotaxis were coated with ECMs, namely, collagen type IV, bovine serum albumin (BSA) and fibronectin, at 1 mg/mL. The results indicate that saratin inhibits the chemotaxis of human monocytes toward MCP-1, or T lymphocytes toward MIP-1α, as determined by in vitro Boyden chamber assay (see FIGS. 1 to 4). The in vitro chemotaxis is a pre-requisite for examining in vivo migration of cells. This inhibition of in vitro chemotaxis of monocytes and T lymphocytes to MCP-1 and MIP-1α with saratin was demonstrated when the filters were coated with 0.01 or 1 mg/mL of the ECMs (see FIGS. 1 to 4). Although, inhibition was most pronounced when the cells were migrating through collagen type IV-coated filters, inhibition was also observed when the filters were coated with BSA or another extracellular matrix protein such as fibronectin. Table 1 summarizes the $IC_{50}$ results for the experiments performed in FIGS. 1 to 4. The ranking of potency inhibiting either cell type when placed on 1 mg/mL substrate is collagen>fibronectin>BSA. Cells tend to differentially use ECM proteins to move and migrate so, without being limited to any theory, the differences in the inhibitory concentrations ($IC_{50}$s) observed with saratin might suggest that the interaction of saratin is on the matrix, and in doing so saratin prevents the interaction of the inflammatory cells with the matrix, and that saratin has no interaction with the inflammatory cells themselves. These results indicate that saratin exerts its inhibitory effect not only when collagen is used but also when other ECM proteins were used. Without being limited to any theory, it is plausible that saratin might bind promiscuously to several proteins. Due to the known effects of saratin blocking the $\alpha_2\beta_1$ integrin binding site for platelets on exposed collagen, it is postulated that other integrin recognition sites on other matrix proteins may be similarly affected.

TABLE 1

Summary of $IC_{50}$ Results from FIG. 1 to 4

| Cell Type | Chemo-attractant | Coating Protein | Coating Conc. (mg) | Saratin IC50 (nM) |
|---|---|---|---|---|
| Monocytes | MCP-1 | Collagen IV | 0.01 | 0.172 |
| | | Collagen IV | 1.0 | 0.0623 |
| | | Fibronectin | 1.0 | 19.4 |
| | | BSA | 1.0 | 1.1 |
| T-lymphocytes | MIP-1α | Collagen IV | 0.01 | 6.863 |
| | | Collagen IV | 1.0 | 0.0079 |
| | | Fibronectin | 1.0 | 3.69 |
| | | BSA | 1.0 | 184.9 |

Figure 5:
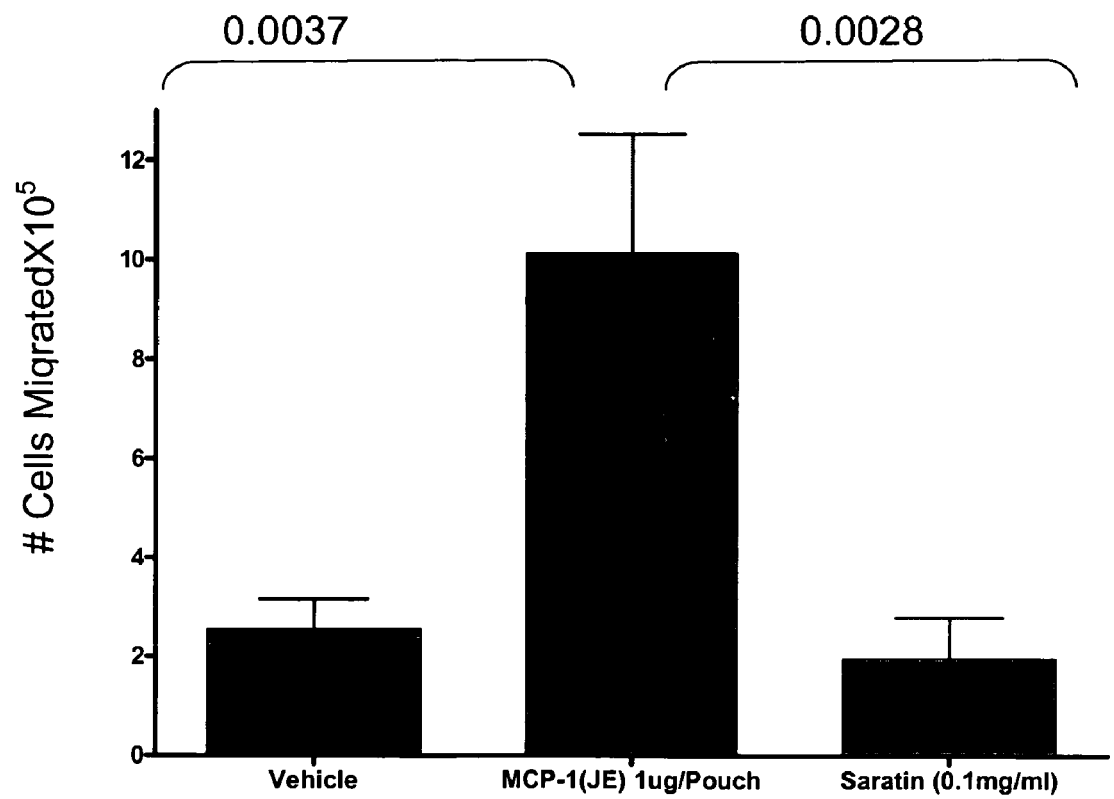
FIG. 5 depicts the effect of saratin on MCP-1(JE)-induced cell migration compared to saline control injected animals in the mouse air pouch model. The group labeled with saratin administration was also induced with MCP-1(JE).
Figure 6:
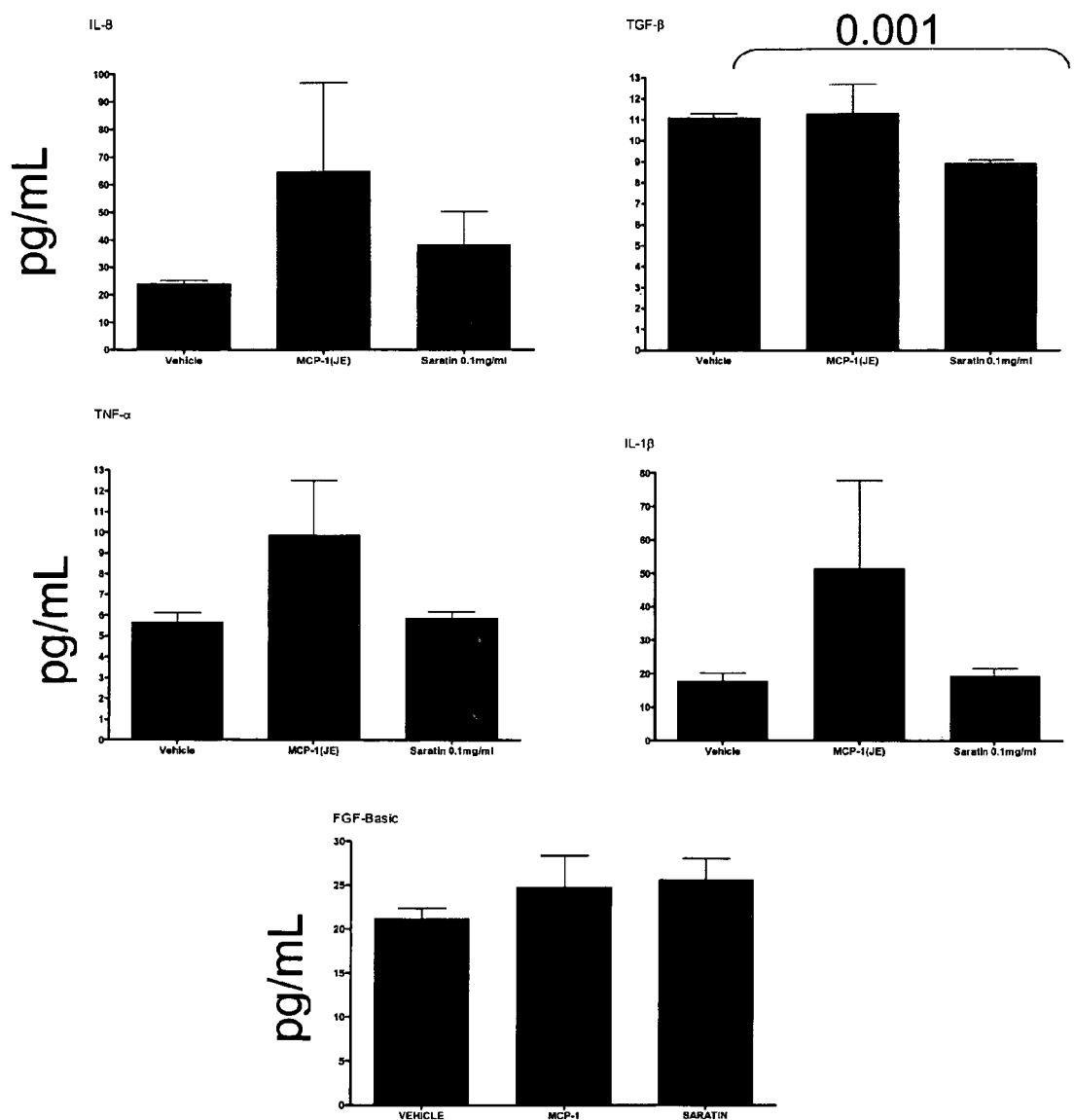
FIG. 6 depicts the effect of saratin on MCP-1(JE)-induced cytokine production compared to saline control injected animals in the mouse air pouch model. The group labeled with saratin administration was also induced with MCP-1(JE) in each case.

In addition to the ability of saratin to inhibit the chemotaxis of monocytes and T lymphocytes in vitro, whether this compound might affect the migration of cells in vivo was examined. Hence, the inflammatory response was mimicked by creating air pouches in the mice injected with the inflammatory cytokine MCP-1. This cytokine is known to recruit monocytes because these cells express the CCR2, the receptor for MCP-1 (*Expert Opin. Ther. Targets* 7:35 (2003)). The results show that MCP-1 induced a migration of cells into the air pouch of mice and saratin inhibited the in vivo migration of cells toward MCP-1 in this air-pouch model (FIG. 5). Although the cell type recruited into the air-pouches was not examined, we assumed that most of the cells are of monocytic lineage since the monocyte-specific chemokine MCP-1 was used for only 2 hours before the number of infiltrating cells was counted. The recruitment of monocytes is usually concomitant with the release of various pro-inflammatory and inflammatory cytokines and chemokines. The results of the studies described herein show that administration of MCP-1 into the air pouches increased the accumulation of IL-8, TNF-α and IL-1β compared to baseline values, however, these increases did not reach statistical significance (FIG. 6). Although administration of saratin decreased the accumulation of the same cytokines induced by MCP-1, these decreases did not reach statistical significance, most likely due to the number of animals used in this study.

No effect of MCP-1 on the secretion of FGF in the air pouch was observed. Similarly, no effect could be demonstrated of saratin on the level of FGF found in naïve mice or mice injected with MCP-1. This may have been the result of the timing of the model in which only 2.5 hours were allowed prior to aspiration of the bleb. Saratin was able to reduce the level of TGF-β found in MCP-1-stimulated animals. This cytokine is pleotropic and has been previously shown to induce the recruitment of mast cells (J. Immunol. 1994, 152: 5860) murine Langerhans cells (J. Immunol. 174:2778 (2005)), leukocytes (Gastroenterology. 122:1122 (2002)), osteoclast (J. Bone Miner. Res. 2001, 16:1237), human monocytes and dendritic cells (J. Immunol. 2000, 164:2285), bone-marrow mesenchymal cells (Exp. Cell Res. 1999, 250: 485), neutrophils (J. Investig. Allergol. Clin. Immunol. 1998, 8:346), and NK cells (Int. Immunol. 1993, 5:825), among other cell types. Due to the variance of the comparator group (stimulated, non-saratin), we are unable to determine if the reduction in TGF-β is due to MCP-1, saratin or both. Whether the ability of saratin to inhibit the in situ migration of cells is due to reducing the level of TGF-β is not clear at the present time. As indicated, saratin also reduced the levels of other cytokines and chemokines which play a role in the recruitment of various cell types. These include IL-8, TNF-α and IL-1β.

In one embodiment, a formulation of saratin prevents cell migration to tissue, including inflammation sites such as injured tissue. In another embodiment, a formulation of saratin prevents T lymphocyte migration to tissue, including inflammation sites such as injured tissue. In yet another embodiment, a formulation of saratin prevents monocyte migration into tissue, including inflammation sites such as injured tissue. In yet another embodiment, a formulation of saratin prevents the production of cytokines involved in inflammation. Without being limited to any theory, the results described herein suggest that saratin may have the ability to decrease cell migration to inflammation sites and as result affect the immune response to tissue injury. For instance, the ability of saratin to decrease cytokine production on an inflammation site suggests that saratin can decrease inflammation by reducing the immune response at that site.

Tendon Injuries

One aspect of the invention is the use of saratin to treat tendon injuries. Preferably, saratin is applied during or after the surgery to treat the injured tendon. Tendons connect muscles to their bony origins and insertions. Tendon repair can be performed using local anesthesia (the immediate area of the surgery is pain-free), regional anesthesia (the local area and surrounding regions near the surgical area are pain-free), or general anesthesia (the patient is unconscious and pain-free). An incision is made over the injured tendon. The damaged or torn ends of the tendon are sewn together. If the tendon has been injured severely, a tendon graft may be required (a piece of tendon from the foot or toe or another part of the body is often used). If necessary, tendons are reattached to the surrounding connective tissue. The area is examined for injuries to nerves and blood vessels, and the incision is closed. The goal of tendon repair is restoration of normal function of joints or surrounding tissues following a tendon laceration. A risk of tendon repair surgery includes formation of scar tissue which prevents smooth movements, e.g., adequate tendon gliding. In one embodiment, saratin would be used to prevent a reduction in gliding which could cause reduced function or increased pain with use.

Repair techniques for lacerated or severed tendons and ligaments ("connective cords" or "cords") vary widely depending on the nature of the injury and the particular cord affected. Examples of often injured cords include flexor tendons of the hand and the anterior cruciate ligament (ACL) of the knee.

Repair of a long flexor tendon that has been severed is typically achieved by suturing the severed tendon ends face-to-face. In one embodiment, saratin is administered to prevent scarring and/or adhesion formation along the length of the tendon during immobilization following the surgery. In cases where an injured flexor tendon is not treated with surgery, saratin is used to prevent scarring during the healing process. In one embodiment, saratin is applied on the entire length of the exposed tendon. In another embodiment, saratin is applied at the interface where the sutures are located.

In the case of an anterior cruciate ligament (connecting the bottom of the femur and the top of the tibia) the stresses resulting from applied forces are much greater, there is less interaction with surrounding tissue and bone, the excursion of the cord is less, and the healing tendencies are vastly different. Saratin is used to promote reconstruction of the ACL when using a bone-tendon-bone graft. Saratin may be used in any of the procedure described above.

Arthroscopic Surgeries and Other Surgeries

Arthroscopy is a surgical procedure in which a camera, attached to a remote light source and video monitor, is inserted into an anatomic joint (e.g., knee, shoulder, etc.) through a small portal incision in the overlying skin and joint capsule. Through similar portal incisions, surgical instruments may be placed in the joint, their use guided by arthroscopic visualization. Such procedures include, for example, partial meniscectomies and ligament reconstructions in the knee, shoulder acromioplasties and rotator cuff debridements and elbow synovectomies. As a result of widening surgical indications and the development of small diameter arthroscopes, wrist and ankle arthroscopies also have become routine.

In one embodiment, a formulation of saratin is peri-operatively applied during arthroscopic surgery. The application encompasses uninterrupted application, repeated application at frequent intervals (e.g., repeated intravascular boluses at frequent intervals intraprocedurally), and applications which are uninterrupted except for brief cessations such as to permit the introduction of products or agents or procedural equipment, such that a substantially constant predetermined concentration is maintained locally at the wound or operative site. In another embodiment, saratin is used as a bathing coat at the end of the procedure, prior to closure, of all surgically injured tissues. In some embodiments, saratin is administered through repeated lavage during surgery or one lavage at the end prior to close.

In addition to arthroscopy, the formulation of saratin may also be applied locally to any human body cavity or passage, operative wound, traumatic wound (e.g., burns) or in any operative/interventional procedure. These procedures include, but are not limited to, urological procedures, gynecological procedures, cardiovascular and general vascular diagnostic and therapeutic procedures, endoscopic procedures and oral, dental and periodontal procedures. In a preferred embodiment, saratin is used along with grafts and devices intended to be implanted. For example, saratin is used to coat a tissue graft or a non-blood containing device prior to implantation. Also, saratin can be applied to the graft or device post-implantation and/or also on the site of surgical injury.

Scar/Keloid Formation

In another aspect of the invention, saratin is used to prevent and/or treat scar and keloid formations. In one embodiment, saratin is administered to inhibit scar tissue resulting from a surgical procedure such as a knee, shoulder or hip arthrotomy or implantation of an orthopedic device, in particular by surgical implant such as a knee, hip, or shoulder replacement or other implanted article. In another embodiment of the invention, the saratin is directly injected into a wrinkle of a patient who has had cosmetic alteration of the wrinkle or applied externally to prevent scar tissue formation. In another embodiment, saratin is administered to inhibit scar tissue resulting from a burn. In yet another embodiment, saratin is used after plastic surgery, reconstructive surgery to prevent or treat scar and keloid formations. For instance, saratin can be used after elective surgery such as head and neck enhancing surgery, breast augmentation or reduction for a better cosmetic outcome.

As used herein, the terms "scar tissue" and "scar tissue formation" include any pathological condition resulting from fibrosis, including keloidosis, fibrocystic conditions and joint stiffness. The terms also include post-surgical adhesions or contractures, keloids, hyperplastic or hypertrophic masses formed following trauma, burns, depressed scars from inflammatory responses including acne, wrinkling, eczema, cellulite formation, neoplastic fibrosis, and other fibrotic conditions involving fibroblast proliferation and metabolism at a localized area in the body. Such localized area may also be referred to herein as a site, situs or biological tissue. Therefore, the methods of the invention, which are directed to the use of saratin for the prevention and reduction of scar tissue formation, also contemplate treatment of conditions involving these pathologies.

In yet another embodiment, post-operative adhesions are treated with saratin, such as after abdominal or pelvic surgery. Injury or inflammation in the peritoneal cavity produces a fibrous exudate. As a result, the serosal surfaces stick together. The fibrous exudate may be absorbed or invaded by fibroblasts to form a permanent fibrous adhesion.

Further, saratin is suitable for the treatment and/or prevention of inflammation and/or adhesions after obstetrics-gynecological procedures. Also, saratin is suitable for treatment and/or prevention of general surgical inflammatory adhesions due to gastric or bowel surgery, and inflammatory-mediated scar formation in plastic surgery. Saratin is useful in scar revision in keloid patients and patients with higher levels of pigment in their skin. This opens up plastic surgery to a whole new group of patients that were contra-indicated previously due to scarring concerns. Prevention of inflammation by saratin may also prevent angiogenesis and also prevent possible stimulation of "dormant" cancer tissues remaining in the affected area.

In cardio-vascular procedures, saratin is useful as a coating for devices such as heart valves, for example, pig heart valves. Further, saratin can be applied on synthetic or mechanical heart valves, direct application by coating stents or agent-eluting stents. Saratin can also be used on indwelling catheters and ports to prevent thrombosis.

In another aspect of the invention, in addition to treatment and/or prevention of platelet-mediated inflammation, saratin can also be used in the treatment and/or prevention white blood cell-mediated inflammation. Not intending to be limited to one mechanism of action, by binding to exposed collagen, fibronectin fibrils or other components of the cellular matrix, saratin could mask white blood cell's (e.g. neutrophils, lymphocytes and monocytes) recognition sites. By blocking white blood cell migration to inflamed tissue, saratin can prevent one of the sources of chemokines that further recruit inflammatory cells. In addition, saratin could directly block leukocyte migration to the injured site and/or prevent its recruitment by decreasing cytokine production at the injured site. Furthermore, not intending to limit the mechanism of action, saratin also inhibits fibroblast migration thus slowing down the process of fibronectin network formation and decreasing or preventing scar formation.

Inflammatory Conditions

In one aspect, saratin is used to treat inflammatory conditions. Without being limited to any mechanism of action, saratin decreases the severity of acute inflammation, while allowing for the laying down of new tissue and, thus, allowing for the healing to progress. Inflammation may play a role in the development of a variety of serious conditions. Inflammation is a process by which our body protects itself from harmful substances such as bacteria and viruses. It is the body's first defense against infection and injury, and it is often accompanied by heat, redness, swelling, and pain. Inflammation can occur in different places in the body: joints, organs, or arteries.

Sometimes our immune system mistakenly triggers an inflammatory response, even when there is no immediate risk of infection.

The role of chemokines and cytokines in inflammatory reactions has been demonstrated by numerous studies. Local administration of a chemokines, e.g., IL-8, by subcutaneous injection results in acute inflammatory reactions which are dominated by neutrophil infiltration. A more delayed mononuclear cell infiltration occurs in response to B chemokines, such as MCP-1, RANTES, and MIP-1α. On the other hand, suppression of chemokines by treatment with neutralizing antibodies has been shown to reduce inflammatory responses. Neutralizing antibodies to IL-8 suppress acute inflammatory reactions due to reperfusion injury, endotoxin-induced arthritis, endotoxin-provoked subcutaneous inflammation, and acute glomerulonephritis (J. Leuk. Biol. 1994; 56: 559-564). Anti-IL-8 also has been shown to reduce delayed-type hypersensitivity reactions (J. Immunol. 1995; 155: 2141-2157). Antibodies to MIP-1α reduce the severity of experimental autoimmune encephalomyelitis (EAE) in mice. Additionally, deletion of the MIP-1α gene in mice reduces the severity of post-Coxsackie-induced myocarditis, but also decreases the resistance of such mice to influenza infection (J. Leuk. Biol. 1996; 59: 61-67), implying that MIP-1α may promote anti-viral host defenses.

Chemokines have been detected in local tissues or bodily fluids by immunohistochemical or enzyme-linked immunoassay techniques, respectively, in a wide variety of inflammatory conditions, as shown in Table 2. MIP-1α and MCP-1 production in the CNS has been correlated with the development of acute clinical disease symptoms in both rat (J Immunol 1993; 150: 2525-2533) and mouse EAE models (J Neuroimmunol 1995; 60:143-150; J Immunol. 1995; 155:5003-5010; FASEB J 1993; 7:592-600). In addition, it has been shown that MIP-1α expression is elevated in the cerebrospinal fluid of MS patients compared with control patients with other neurological diseases, and the increased levels correlated with increased CSF leukocyte counts (J. Neurol. Sci. 1995; 129:223-227). Furthermore, recent studies have shown that MIP-1α regulates the immunopathogenesis of EAE during acute disease and MCP-1 regulates the relapsing phase of disease. This differential regulation appears to result from MIP-1α being produced primarily by infiltrating macrophages and T lymphocytes whereas MCP-1 is produced primarily by CNS resident astrocytes (ILAR Journal 1999; 40(4)).

In another example of the role of cytokines in inflammatory conditions, recent results suggest that that RANTES, MIP-1α, and MCP-1 may regulate cell trafficking in asthma in response to allergen exposure (Am. J. Respir. Crit. Care Med., 1997; 156 (5), 1377-1383).

Further, in other embodiments saratin is used for the treatment of obstructive pulmonary disease. This is a disease state characterized by airflow limitation that is not fully reversible. The airflow limitation is usually both progressive and associated with an abnormal inflammatory response of the lungs to noxious particles or gases. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, saratin is used for the treatment of asthma. Asthma is a disease of the respiratory system in which the airways constrict, become inflamed, and are lined with excessive amounts of mucus, often in response to one or more triggers, such as exposure to an environmental stimulant (or allergen), cold air, exercise, or emotional stress.

Also, saratin may be used for the treatment of endotoxemia and sepsis. Sepsis is a medical condition, resulting from the immune response to an infection. Septicemia is sepsis of the bloodstream caused by bacteremia, which is the presence of bacteria in the bloodstream. The term septicemia is also used to refer to sepsis in general. The immunological response that causes sepsis is a systemic inflammatory response causing

TABLE 2

Chemokines Detected at Disease States

| Disease States | Site | Chemokine |
| --- | --- | --- |
| Cystic Fibrosis | Lavage Fluid | IL-8, ENA-78, MCP-1 |
| Acute Pulmonary Diseases | Tissue | IL-8, ENA-78, MCP-1, Rantes |
| Asthmatic Reactions | Lavage Fluid | MCP-1, MIP-1α, Rantes |
| Endotoxemia and Sepsis | Plasma | IL-8, MIP-1α, MCP-1, Rantes |
| Rheumatoid Arthritis | Synovial Fluid | IL-8, ENA-78, MCP-1, MIP1α |
| Osteoarthritis | Synovial Fluid | MCI-1β |
| Psoriatic Scale | Tissue Extract | IL-8, GROα,β,γ, MCP-1, IP-10, ENA-78 |
| Gastrointestinal Inflammation | Tissue | IL-8, MCP-1, MIP1α/β, Rantes, IP-10 |
| Arteriosclerosis | Tissue | MCP-1, MIP1α/β, Rantes, IL-8, GROβ |
| Immune Complex Glomerulonephritis | Tissue | IL-8, MCP-1 |
| Uveoretinitis | Tissue | IL-8, IP-10, MCP-1, Rantes, MIP-1α/β |
| Tuberculoid Leprosy | Tissue | IP-10 |
| Post-Major Surgery | Plasma | IL-8 |
| Wound Healing Site | Tissue | MCP-1 and IP-10 |
| Cytomegalovirus Encephalomyelitis | Cerebrospinal Fluid | MCP-1 |
| Atopic and Contact Dermatitis | Tissue | Rantes, Eotaxin, IL-8, MCP-1, IP-10 |

In some embodiments, saratin is used for the treatment of an inflammatory condition. For instance, saratin can be used to treat encephalomyelitis. Encephalomyelitis is a general term for inflammation of the brain and spinal cord, describing a number of disorders: (i) acute disseminated encephalomyelitis or postinfectious encephalomyelitis, a demyelinating disease of the brain and spinal cord, possibly triggered by vaccination or viral infection; (ii) encephalomyelitis disseminata, a synonym for multiple sclerosis, a disorder of the central nervous system (brain and spinal cord) characterized by decreased nerve function due to myelin loss and secondary axonal damage; (iii) equine encephalomyelitis, a potentially fatal mosquito-borne viral disease that infects horses and humans; (iv) myalgic encephalomyelitis, a syndrome involving inflammation of the central nervous system with symptoms of muscle pain and fatigue; the term has sometimes been used interchangeably with chronic fatigue syndrome; and (v) experimental autoimmune encephalomyelitis (EAE), an animal model of brain inflammation. In some embodiments, saratin is locally applied by intrathecal or epidural injections.

widespread activation of inflammation and coagulation pathways. Endotoxemia is caused by the presence of endotoxins in the blood, which, if derived from gram-negative rod-shaped bacteria, may cause hemorrhages, necrosis of the kidneys, and shock.

In one embodiment, saratin is used to for the treatment of rheumatoid arthritis (RA). RA is an autoimmune disorder that causes the body's immune system to attack the bone joints. In another embodiment, saratin is used for the treatment of psoriasis, a skin disorder in which rapidly-multiplying skin cells produce itchy, scaly inflamed patches on the skin. In yet another embodiment, saratin is used for the treatment of contact or atopic dermatitis. Contact dermatitis is an inflammation of the skin, which occurs when the skin comes in contact with substances to which the skin is sensitive or allergic. Allergic contact dermatitis can appear after initial or prolonged exposure to an irritant. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

In addition, saratin may be used to treat acne.

In addition, saratin may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further, saratin may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, saratin may be used for the treatment of bursitis, lupus, acute disseminated encephalomyelitis (ADEM), addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barré syndrome (GBS), hashimoto's disease, inflammatory bowel disease, lupus erythematosus, myasthenia gravis, opsoclonus myoclonus syndrome (OMS), optic neuritis, ord's thyroiditis,ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradentitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

Combination Therapies

Saratin can be used in the disclosed methods in combination with other suitable agents. For example, saratin can be used with the agents described herein. Several inhibitors which prevent platelet adhesion are monoclonal antibodies directed to vWF. It has as well been suggested that glycoprotein IIb/IIIa inhibitors may be beneficial in inhibiting platelet adhesion. Some of these inhibitors like the monoclonal Ab c7E3 have already been tested clinically while others like the KGD- and RGDF-inhibitors are still under study.

A source for the screening of new compounds that interfere with collagen induced platelet adhesion is given in nature through blood-sucking animals. Several inhibitors have been isolated from nature as described in the literature: A 65 kDa protein called Calin isolated from *Hirudo medicinalis* (U.S. Pat. No. 5,587,360 WO 92/07005) (Munro, R. et al., Blood Coagulation and Fibrinolysis, 1991, 2, 179-184) and a 16 kDa (LAPP) protein isolated from the salivary glands of the leech *Haementera officinalis* (U.S. Pat. No. 5,324,715). Both proteins have been described as aggregation inhibitors as tested in static assays of collagen dependent platelet aggregation.

The soft tick, *Omithodoros moubata*, also contains an anti-platelet protein (Moubatin) which is active in preventing collagen-stimulated platelet aggregation (Waxman, L. et al.; J. Biol. Chem., 1993, 268, 5445-49). Another inhibitor of platelet aggregation from a blood-sucking bug was disclosed in WO 9309137 by Noeske-Jungblut C. et al. A 50 kDa protein was isolated from snake venom and a 19 kDa protein was isolated from the saliva of *Triatoma pallidipennis*, a blood-sucking bug. The protein was found to contain a factor that specifically inhibits collagen-induced platelet aggregation. The 19 kDa protein named pallidipin inhibits collagen-mediated aggregation of platelets in plasma Gan et al. described Echistatin as an inhibitor binding to the fibrinogen receptor GP IIa/IIIb (J. Biol. Chem, 1988, 263, 19827-32).

Examples for use in coronary-artery applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

Saratin may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin.

Saratin may be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which may be administered in conjunction with saratin include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament.

Saratin can be used in combination with the agents disclosed herein or other suitable agents, depending on the condition being treated. When used in combination therapy, saratin may be administered with the second agent simultaneously or separately. This administration in combination can include simultaneous administration of the two agents in the same dosage form, simultaneous administration in separate dosage forms, and separate administration. That is, saratin and any of the agents described above can be formulated together in the same dosage form and administered simultaneously. Alternatively, saratin and any of the agents described above can be simultaneously administered, wherein both the agents are present in separate formulations. In another alternative, saratin can be administered just followed by and any of the agents described above, or vice versa. In the separate administration protocol, saratin and any of the agents described above may be administered a few minutes apart, or a few hours apart, or a few days apart.

Formulations and Coatings

Saratin compounds described herein are usually administered in the form of therapeutic compositions. The saratin compounds of the invention can be incorporated into therapeutic compositions suitable for administration to human. This invention therefore provides therapeutic compositions that contain, as the active ingredient, one ore more saratin compounds or a modified version as described herein, or a therapeutically acceptable salt and/or coordination complex thereof, and one or more therapeutically acceptable excipients, carriers, including inert solid diluents and fillers, diluents, including sterile aqueous solution and various organic solvents, permeation enhancers, solubilizers and adjuvants. Such compositions are prepared in a manner well known in the art.

The saratin polypeptides according to the invention may form therapeutically acceptable salts with any non-toxic, organic or inorganic acid. Inorganic acids are, for example, hydrochloric, hydrobromic, sulphuric or phosphoric acid and acid metal salts such as sodium monohydrogen orthophosphate and potassium hydrogen sulfate. Examples for organic acids are the mono, di and tri carboxylic acids such as acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic and sulfonic acids such as methane sulfonic acid. Salts of the carboxy terminal amino acid moiety include the non-toxic carboxylic acid salts formed with any suitable inorganic or organic bases. These salts include, for example, alkali metals such as sodium and potassium, alkaline earth metals such as calcium and magnesium, light metals of Group IIIA including aluminum, and organic primary, secondary and tertiary amines such as trialkylamines, including triethylamine, procaine, dibenzylamine, 1-ethenamine, N,N'-dibenzylethylene-diamine, dihydroabietylamine and N-alkylpiperidine.

The saratin polypeptides according to the invention may be covalently modified. These covalent modifications are useful, for instance, in stabilizing the saratin polypeptides of the inventions in the therapeutic compositions described herein or in vivo after administration. One type of covalent modification includes linking the peptides of the invention to one of a variety of nonproteinaceous polymers, e.g., polyethylene glycol (PEG), polypropylene glycol, or polyoxyalkylenes, in the manner known in the art.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group. Another type of modification includes artificial hydrophilization of the surface area of the peptides by transforming tyrosine residues to aminotyrosines or by adding carboxylic into lysine residues. Other modifications include the formation of saratin peptides-oligoamine complexes. Another type of covalent modification of the peptides of the invention comprises the addition of glycosylation sites. Methods to perform the modifications described herein are well known in the art.

A therapeutic composition of the invention is formulated to be compatible with its intended route of administration. Examples of routes of administration include, but are not limited to, oral, buccal, intravenous, parenteral, inhalation, rectal, intradermal, subcutaneous, transmucosal, transdermal, pulmonar, intra-articular, intratracheal, intramuscular, intrasternal, nasal or topical administration. Topical administration may also involve the use of transdermal administration such as transdermal patches or iontophoresis devices. The present invention further provides the use of saratin peptides of the present invention via local delivery devices/catheters or via stents and stent coatings and vascular grafts and graft coating technologies.

The route of administration will be selected based on the compound being administered, the status of the patient and disease that is being treated. A compound may be administered through different routes depending on the severity of the disease or the type or therapeutic intervention, e.g. emergency situations may require intravenous administration, acute but not life threatening situation may be treated orally, while treatment after surgical procedure can be administered by a stent or catheter-based device.

Therapeutic compositions may be formulated in conventional manner using one or more physiologically acceptable carriers comprising excipients and auxiliaries which facilitate processing of the active compounds into preparations which can be used therapeutically. Proper formulation is dependent upon the route of administration chosen and standard therapeutic practice. As used herein, the term "therapeutically acceptable carrier" means an inert, non toxic solid or liquid filler, diluent or encapsulating material, not reacting adversely with the active compound or with the patient. Suitable, liquid carriers are well known in the art such as sterile water, saline, aqueous dextrose, sugar solutions, ethanol, glycols and oils, including those of petroleum, animal, vegetable, or synthetic origin, for example, peanut oil, soybean oil and mineral oil.

Saratin peptides of the invention may be complexed with other agents as part of their being therapeutically formulated. The therapeutic compositions may take the form of, for example, tablets or capsules prepared by conventional means with therapeutically acceptable excipients such as binding agents (e.g., acacia, methylcellulose, sodium carboxymethylcellulose, polyvinylpyrrolidone (Povidone), hydroxypropyl methylcellulose, sucrose, starch, and ethylcellulose); fillers (e.g., corn starch, gelatin, lactose, acacia, sucrose, microcrystalline cellulose, kaolin, mannitol, dicalcium phosphate, calcium carbonate, sodium chloride, or alginic acid); lubricants (e.g. magnesium stearates, stearic acid, silicone fluid, talc, waxes, oils, and colloidal silica); and disintegrators (e.g. micro-crystalline cellulose, corn starch, sodium starch glycolate and alginic acid. If water-soluble, such formulated complex then may be formulated in an appropriate buffer, for example, phosphate buffered saline or other physiologically compatible solutions. Alternatively, if the resulting complex has poor solubility in aqueous solvents, then it may be formulated with a non ionic surfactant such as TWEEN™, or polyethylene glycol. Thus, the compounds and their physiologically acceptable solvates may be formulated for administration.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Therapeutic compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The composition preferably is sterile and should be fluid to the extent that easy syringability exists. The compositions suitably should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., saratin compound) in a therapeutically effective or beneficial amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

The present invention further provides the use of saratin and derivatives via local delivery devices/catheters or via stents and stent coatings and vascular grafts and graft coating technologies, for example. The invention also provides methods of administering saratin in compositions that elute out regulated quantities of the saratin over time in a localized area.

In particular, one embodiment of the present invention relates to uses of catheter-based devices to deliver saratin locally. Saratin may as well be applied with or without other therapeutic agents out of a polymer matrix into body tissues using catheters. The basic requirements for the polymer material to be used in the present method are biocompatibility and agent release properties which can be adapted to the specific application.

The local controlled saratin release may be achieved by permeation only, iontophoresis only, electroporation only, or combined iontophoresis and electroporation may be used to release and incorporate saratin efficiently inside the vessel lumen. Preferably, the catheter is able to perform procedures designed to maintain a high concentration of therapeutic agent in the selected vessel space such that the results give an improved vessel coating with saratin alone or with additional treatment agents.

The present invention is particularly applicable to the local delivery of saratin during and after interventional cardiology procedures such as angioplasty and stent implantation and endarterectomy.

In a preferred aspect, the invention is an implant coated with saratin. The implant may be partially or completely coated with saratin. Typically, the implant is a medical device. Implants can also include biological implants, such as organs, tissues, or cell transplants. Saratin may also be applied to the site of surgery. It is an embodiment of the invention that the stent or catheter-based devices are provided with a saratin peptide according to the invention by way of at least partially coating the stent or catheter-based devices with a composition comprising a polymer. A polymer according to the present invention is any that facilitates attachment of the saratin peptide(s) to the stent or catheter-based device and/or facilitates the controlled release of saratin. Polymers may be, for example, film-forming polymers that are absorbable or nonabsorbable. The polymer may be biostable or bioabsorbable depending on the desired rate of release or the desired degree of polymer stability.

Suitable bioabsorbable polymers that could be used include, but are not limited to, polymers selected from the group consisting of aliphatic polyesters, poly(amino acids), copoly(ether-esters), polyalkylenes oxalates, polyamides, poly(iminocarbonates), polyanhydrides, polyorthoesters, polyoxaesters, polyamidoesters, polylactic acid (PLA), polyethylene oxide (PEO), polycaprolactone (PCL), polyhydroxybutyrate valerates, polyoxaesters containing amido groups, poly(anhydrides), polyphosphazenes, silicones, hydrogels, biomolecules and blends thereof.

Other polymeric biomolecules for the purpose of this invention, preferably that are not a target for saratin, include naturally occurring materials that may be enzymatically degraded in the human body or are hydrolytically unstable in the human body such as gelatin, glycosaminoglycans and absorbable biocompatible polysaccharides such as chitosan, starch, fatty acids (and esters thereof), glucoso-glycans and hyaluronic acid.

Suitable biostable polymers with relatively low chronic tissue response, such as polyurethanes, silicones, poly(meth)acrylates, polyesters, polyalkyl oxides (polyethylene oxide), polyvinyl alcohols, polyethylene glycols and polyvinyl pyrrolidone, as well as, hydrogels such as those formed from crosslinked polyvinyl pyrrolidinone and polyesters could also be used. Other polymers could also be used if they can be dissolved, cured or polymerized on the stent or catheter-based device. These include polyolefins, polyisobutylene and ethylenealphaolefin copolymers; acrylic polymers (including methacrylate) and copolymers, vinyl halide polymers and copolymers, such as polyvinyl chloride; polyvinyl ethers, such as polyvinyl methyl ether; polyvinylidene halides such as polyvinylidene fluoride and polyvinylidene chloride; polyacrylonitrile, polyvinyl ketones; polyvinyl aromatics such as polystyrene; polyvinyl esters such as polyvinyl acetate; copolymers of vinyl monomers with each other and olefins, such as etheylene-methyl methacrylate copolymers, acrylonitrile-styrene copolymers, ABS resins and ethylene-vinyl acetate copolymers; polyamides such as Nylon 66 and polycaprolactam; alkyd resins; polycarbonates; polyoxymethylenes; polyimides; polyethers; epoxy resins, polyurethanes; rayon; rayontriacetate, cellulose, cellulose acetate, cellulose acetate butyrate; cellophane; cellulose nitrate; cellulose propionate; cellulose ethers (i.e. carboxymethyl cellulose and hydoxyalkyl celluloses); and combinations thereof.

Other polymers suitable for use in the present invention are bioabsorbable elastomers, e.g., aliphatic polyester elastomers. In the proper proportions aliphatic polyester copolymers are elastomers. Elastomers present the advantage that they tend to adhere well to a metal stents and can withstand significant deformation without cracking.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

In one embodiment the coating is made from a hydro-gel, such as poly-ethylene oxide, albumin, hydrophilic polymethacrylates and hydrophilic poly urethanes.

Anti thrombotic and anti restenosis coatings are in general biocompatible coatings that may also serve as reservoirs for local agent delivery. The coatings are mainly based on hydrogels and examples in the patent literature of methods for preparing various types of hydrogels and coating medical devices include WO9211896, WO9811828, WO0147572, EP0887369 and WO0139811.

The release profile of the therapeutic substances that are contained within the coating can be adjusted for example by varying the thickness of polymer layers or by selecting specific polymeric coatings that contribute selected physicochemical properties (such as charge, hydrophobicity, hydrophilicity) and or by preparing the coating as different layers. The criteria for selection of the polymer and the optimization of release rate are understood by one of ordinary skill in the art. Other coatings are described by Fischell (Circulation, 1996, 94:1494-95), Topol et al (Circulation, 1998, 98:1802-20) and McNair et al in device Technology, 1996, 16-22.

Ideally saratin treatment may be administered simultaneously with the appropriate therapeutic intervention which may be achieved by incorporating saratin into the coating of a surgical device. Another aspect could also involve the direct coating of the injured tissues with saratin.

Additionally, normal saratin delivery means may be used in the invention as well, such as free fluid form, including combinations with other therapeutic agents. Preferably, polymer/hydrogel matrices are used. A general technical solution to the local application of saratin either on a medical device or as a coating to the injured tissue is for example the incorporation of saratin into a polymer or hydrogel coating.

With respect to the polymer composition, the term "hydrogel" as used herein includes synthetic polymers with pores or interstices of different sizes and capacities and varying physicochemical properties especially with respect to the charge or the hydrophilic/hydrophobic nature of the gel matrix which may be introduced during manufacture of the coating or coated device. A variety of synthetic elastomers and naturally occurring polymeric materials are known to those skilled in the art. Saratin can be incorporated in the matrix either during polymer production or added after coating or molding of the polymer into the desired shape. Additionally, many of a number of different polymeric materials and methods of fabrication may be used to form the polymer matrices used in the present invention. Examples of suitable polymer materials or combinations include, but are not limited to, biocompatible and/or biodegradable polymers. Several alkyl alkyl- and cyanoacrylates have been investigated for surgical use and some isobutyl cyanoacrylates have been found especially suitable.

A typical hydrogel polymer may be produced from a monomer mixture comprising 40-60 parts by weight of a purified monoester of a hydroxyalkyl alkyl acrylate having a single olefinic double bond, 40-60 parts by weight of a methacrylic monomer containing one olefinic double bond, and 0.001-5 parts by weight of a polymerization initiator. Polymerization may be accomplished by the conventional techniques of bulk polymerization, solution polymerization, suspension polymerization or emulsion polymerization. The polymerization technique used is dependent upon the volume of polymer required and the nature of the final product being produced. A typical hydrogel product would be described by a molar ratio of monoester to methacrylic monomer within the range of 1:1 to 2.3:1, preferably 1.5:1, wherein the pore diameter of the polymer is greater than 90 Angstroms. As the monoester of a hydroxyalkyl acrylate having a single olefinic double bond, acceptable compounds include, but are not limited to, 2-hydroxyethyl methacrylate, glyceryl methacrylate, 2-hydroxypropyl methacrylate, glycidyl methacrylate, 2-hydroxyethyl acrylate, and 2-hydroxypropyl acrylate. Acceptable methacrylic monomers are methacrylic acid, methacrylamide 5 and methacrylonitrile. The polymerization initiator may depend on the method of polymerization or the final intended use of the polymer. For example, where the polymer is to be formed as a solid object, free radical initiators may be used. Preferred initiators of that type include difunctional polyesters such as 2,5-Dimethyl-2,5-bis(2ethylhexoylperoxy)hexane, or tertiarybutyl peroxypivilate. Alternatively, where the ultimate use of the polymer is as a coating applied in the form of the monomer mixture and polymerized in situ, the initiator may be radiation activated such as UV catalysts 2,2Azobis(2-methylpropionitrile) or azobisbutyronitrile (AIBN). The initiators are not restricted to use in a particular polymerization method or for a particular final product. For example, the free radical initiators may be employed in coatings and the radiation activated initiators may be employed in the formation of solid articles. In addition to the substantially similar fractions of the monoester and methacrylic monomer, the monomer mixture may be enhanced with trace amounts of a longer chain alkyl acrylate or methacrylate ester co-monomer such as cyclohexyl methacrylate, trimethylolpropane trimethacrylate or ethyleneglycol dimethacrylate. Such additional co-monomers enhance the polymer crosslinking for situations where added polymer strength is desired. The trace amounts of these comonomers are generally less than 0.1% by weight of the total monomer mixture. The hydrogel polymers used in the present invention may be formed to produce an article which is sufficiently crosslinked by intrinsic action that the resulting article requires no additional crosslinking monomers. Additional examples for biodegradable polymers are poly(lactides), polyglycolides, polyanhydrides, polyorthoesters, polyactals, polydihydropyrans, polycyanoacrylates and copolymers of these and polyethylene glycol. These can take the form of co-polymer hydrogels or cross-linked polymer networks into which agents for enhanced local delivery can be incorporated either during polymerization or, in the case of certain hydrogels, loaded subsequently. Preferable matrices would be tailored according to the molecular characteristics of the agent to control free diffusion outwards.

Delayed release and extended release compositions can be prepared. The delayed release/extended release therapeutic compositions can be obtained by complexing an agent with an acceptable ion-exchange resin and coating such complexes, or by including in the composition one or more slow release agents to facilitate slow release of the saratin peptides of the invention. Example of slow release agents include, but are not limited to, magnesium alloys, poly(glycolic) acid, poly(lactic acid) or in general glycolic- and lactic acid based polymers, copolymers, poly caprolactones and in general, poly hydroxyl alkanoates poly(hydroxy alcanoic acids), Poly(ethylene glycol), poly vinyl alcohol, poly(orthoesters), poly(anhydrides), poly(carbonates), poly amides, poly imides, poly imines, poly(imino carbonates), poly(ethylene imines), polydioxanes, poly oxyethylene(poly ethylene oxide), poly(phosphazenes), poly sulphones, lipids, poly acrylic acids, poly methylmethacrylate, poly acryl amides, poly acrylo nitriles (Poly cyano acrylates), poly HEMA, poly urethanes, poly olefins, poly styrene, poly terephthalates, poly ethylenes, poly propylenes, poly ether ketones, poly vinylchlorides, poly fluorides, silicones, poly silicates (bioactive glass), siloxanes (Poly dimethyl siloxanes), hydroxyapatites, lactide-capronolactone, natural and non natural poly aminoacids, poly b-aminoesters, albumines, alginates, cellulose/cellulose acetates, chitin/chitosan, collagene, fibrine/fibrinogen, gelatine, lignine, proteine based polymers, Poly(lysine), poly (glutamate), poly (malonates), poly(hyaluronic acids), Poly nucleic acids, poly saccharides, poly(hydroxyalkanoates), poly isoprenoids, starch based polymers, copolymers thereof, linear, branched, hyperbranched, dendrimers, crosslinked, functionalized derivatives thereof, or hydrogels based on activated polyethyleneglycols combined with alkaline hydrolyzed animal or vegetal proteins.

In addition, combinations of immediate release compositions and delayed release/extended release compositions may be formulated together.

Oral liquid preparations may be in the form of aqueous or oily suspensions, solutions, emulsions, syrups or elixirs, containing, together with the active compound(s), wetting agents, sweeteners, and coloring and flavoring agents or may be presented as a dry product for reconstitution with water or another suitable vehicle before use. Such liquid preparations may contain conventional additives like suspending agents, emulsifying agents, non-aqueous vehicles and preservatives. Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. Various liquid and powder formulations can be prepared by conventional methods for inhalation by the patient.

Oral compositions generally include an inert diluent or an edible carrier. Suitable oral compositions may be e.g., enclosed in gelatin capsules or compressed into tablets. Tablets, troches and capsules for oral administration contain conventional excipients such as binding agents, fillers, diluents, tableting agents, lubricants, disintegrants, and wetting agents. The tablets may be coated according to methods well known in the art. Oral compositions can also be prepared using a fluid carrier for use as a mouthwash, wherein the compound in the fluid carrier is applied orally and swished and expectorated or swallowed. Therapeutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Topical applications may be in the form of aqueous or oily suspensions, solutions, emulsions, jellies or emulsion ointments. The topical composition may be in the form of a therapeutic but it does not have to be. For example, it can be a cosmetic. In one embodiment of the invention, a locally administrable topical composition is provided. The locally administrable topical composition includes a topical carrier. The topical carrier is one which is generally suited to topical agent administration and includes any such materials known in the art. The topical carrier is selected so as to provide the composition in the desired form, e.g., as a liquid, lotion, cream, paste, gel, powder, or ointment, and may be comprised of a material of either naturally occurring or synthetic origin. It is essential that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

The saratin polypeptides according to the present invention are suitable as therapeutically effective compounds in therapeutic compositions and combinations. The therapeutic formulations according to the invention optionally may comprise additional active ingredients like aspirin, anticoagulants such as hirudin or heparin or thrombolytic agents such as plasminogen activator or streptokinase or any other agent including those described herein.

The formulations according to the invention may be administered as unit doses containing conventional non-toxic therapeutically acceptable carriers, diluents, adjuvants and vehicles which are typical for the selected route of administration.

Unit doses according to the invention may contain daily required amounts of the saratin peptides according to the invention, or sub-multiples thereof to make up the desired dose. The optimum therapeutically acceptable dosage and dose rate for a given patient (mammals, including humans) depends on a variety of factors, such as the activity of the specific active material employed, the age, body weight, general health, sex, diet, time and route of administration, rate of clearance, the object of the treatment, e.g., therapy or prophylaxis and the nature of the thrombotic disease to be treated. The dose according to the invention need not remain constant but can be adjusted according to parameters that are well known to those of skill in the art. In addition, the dose according to the invention can be sub- or supra-therapeutic.

In one embodiment the therapeutically effective dose of the peptides of this invention is between about 0.001 and 100 mg/kg body weight, preferably between 0.01 and 10 mg/kg body weight. In one embodiment, the dose of the peptides of this invention is 0.33 mg/kg body weight.

In one embodiment, for vascular applications, the formulation comprises about 0.1 mg/mL to about 30 mg/mL of saratin. In another embodiment, the formulation for vascular applications comprises about 0.1 mg/mL to about 1 mg/mL of saratin, about 1 mg/mL to about 5 mg/mL of saratin, about 5 mg/mL to about 10 mg/mL of saratin, about 10 mg/mL to about 15 mg/mL of saratin, about 15 mg/mL to 20 mg/mL of saratin, about 20 mg/mL to about 25 mg/mL of saratin, or about 25 mg/mL to about 30 mg/mL of saratin. In a preferred embodiment, the formulation for vascular applications comprises about 1 mg/mL to about 5 mg/mL of saratin. For non-vascular applications, the formulation comprises about 0.01 mg/mL to about 20 mg/mL of saratin. In one embodiment, the formulation for non-vascular applications comprises about 0.01 mg/mL to about 0.1 mg/mL of saratin, about 0.1 mg/mL to about 1 mg/mL of saratin, about 1 mg/mL to about 5 mg/mL of saratin, about 5 mg/mL to about 10 mg/mL of saratin, about 10 mg/mL to about 15 mg/mL of saratin, or about 15 mg/mL to 20 mg/mL of saratin. In a preferred embodiment, the formulation for non-vascular application comprises about 0.1 mg/mL to about 1 mg/mL of saratin. Typically, the amount of formulation used will depend on the dose desired at the site of application. Doctors may apply an excess amount of formulation and then remove the excess amount, by sponging or lavage, to reach the desired concentration.

In another embodiment, 0.1 mg/mL to 20 mg/mL of saratin is applied for vascular use in a volume sufficient to cover the intended area. In one embodiment, 1 mg/mL to 5 mg/mL, 5 mg/mL to 10 mg/mL, or 10 mg/mL to 20 mg/mL of saratin is applied for vascular use in an amount sufficient to cover the intended area. In a preferred embodiment, 1 mg/mL to 5 mg/mL of saratin is applied for vascular use in an amount sufficient to cover the intended area. In another embodiment, 0.01 mg/mL to 10 mg/mL of saratin is applied for non-vascular use in an amount sufficient to cover the intended area. In one embodiment, 0.01 mg/mL to 5 mg/mL, or 5 mg/mL to 10 mg/mL of saratin is applied for vascular use in an amount sufficient to cover the intended area. In a preferred embodiment, 0.01 mg/mL to 5 mg/mL of saratin is applied for non-vascular use in an amount sufficient to cover the intended area. One of ordinary skill in the art would understand that in some embodiments a higher local concentration may need to be applied to reach the effective concentration because some of the therapeutic agent may be lost, for example, due to flush or sponge removal. In addition the therapeutic effective dose of saratin may vary when use is combination with other therapeutic agents such as thrombin inhibitors or anticoagulants.

It is also object of this invention to provide an implantable or extracorporeal medical device for use in contact with body fluids in order to render the device surface substantially thromboresistant, coated with an immobilized polypeptide as defined above and in the claims. The polypeptide according to the invention is immobilized on a medical device so as to render the surface biocompatible and thromboresistant. Such devices sometimes have surfaces properties which typically induce platelet aggregation, which is a disadvantage in their intended uses in implantable and extracorporeal devices in contact with blood or other body fluids. Examples for such devices which are commonly made from plastics materials and synthetic fibres are protheses, artificial organs, ocular lenses, sutures, artificial vascular segments, catheters, dialysers, tubes and vessels carrying blood.

A preferred formulation is a simple phosphate buffered saline and the orthopedic applications use a formulation with more viscosity, such as formulations with hydrogels. Suitable formulations can be about 0.01 mg/mL to about 0.1 mg/mL of saratin, about 0.1 mg/mL to about 1 mg/mL of saratin, about 1 mg/mL to about 5 mg/mL of saratin, about 5 mg/mL to about 10 mg/mL of saratin, about 10 mg/mL to about 15 mg/mL of saratin, about 15 mg/mL to 20 mg/mL of saratin, about 20 mg/mL to about 25 mg/mL of saratin, about 25 mg/mL to about 30 mg/mL of saratin, about 30 mg/mL to about 40 mg/mL of saratin, or about 40 mg/mL to about 50 mg/mL of saratin in PBS or a hydrogel or other suitable vehicles. The material may be stored frozen, refrigerated, or as a lyophilized powder.

EXAMPLES

Example 1

Use of Saratin in a Canine Flexor Tendon Repair Model

Tendon injury in the finger remains a clinical challenge to hand surgeons. A canine model is commonly used to study biological effects of tendon injuries and their treatment.

The purpose of this study is to evaluate the effect of saratin on the outcome following flexor tendon repair in an in vivo canine model. Following tendon injury in the canine flexor tendon repair model, saratin is applied in a gel formulation or as a simple liquid at the site of the injury. In a control group, the gel or liquid control (without saratin) is applied. Work of flexion (WOF) and tendon strength is evaluated following tendon laceration and repair in the dogs sacrificed 10 days postoperatively. It is expected that in the dogs treated with saratin, the WOF and tendon strength are greater and there is reduced scarring.

Example 2

Saratin Facilitates Wound Healing and Scar Formation

Mice Model

The effect of saratin on wound healing is determined in mice. The wounds are produced by fine surgical scissors and consist of 4 mm full thickness skin incisions. A sterile adhesive bandage is used to cover each wound. Following formation of the wound, saratin is applied on the incision. New vessel formation at each wound site is assessed using magnetic resonance microimaging (MRI) on days 0, 1, 2, 3, and 5 after the injury. Treatment with saratin will diminish the massive neovascularization that surrounds the wound on days 1-2 after injury, accelerates wound healing, and minimizes scarring.

Visual observation of wounds will also provide evidence of the benefits of saratin treatment. The animal treated with saratin will present little evidence of scarring as compared to the control animal at a later time point.

Wound disruption strength, or tissue tensile strength across a wound, is evaluated in the mice. Full thickness skin incisions are made on the right lumbar region followed by topical application of saratin on the wound. The force needed to disrupt the wound is measured at 40 hours and 7 days after incision. Animals treated with saratin will demonstrate significant increases relative to controls in the strength of the healing wounds.

Yucatan Pig Model

The effect of saratin in wound healing and scar formation can also be determined using Yucatan pigs. The swine's skin is considered physiologically similar to human skin.

Four sets of surgical wounds can be induced on each animal. Each set can consist of three lesions: (1) a partial-thickness lesion (1 cm$^2$), (2) a full-thickness lesion (1 cm$^2$), and (3) an incisional wound (4 cm). These surgical wounds simulate acute superficial wounds (e.g., abrasions, full-thickness pressure sores, ulcers) and postsurgical incisions or lacerations. A sterile adhesive bandage is used to cover each wound.

Following formation of the wound, saratin is applied on the incision. New vessel formation at each wound site is assessed using magnetic resonance microimaging (MRI) on days 0, 1, 2, 3, and 5 after the injury. Treatment with saratin will diminish the massive neovascularization that surrounds the wound on days 1-2 after injury, accelerates wound healing, and minimizes scarring.

Visual observation of wounds will also provide evidence of the benefits of saratin treatment. The animal treated with saratin will present little evidence of scarring as compared to the control animal at a later time point.

Wound disruption strength, or tissue tensile strength across a wound, is evaluated in the pigs. Full thickness skin incisions are made on the right lumbar region followed by topical application of saratin on the wound. The force needed to disrupt the wound is measured at 40 hours and 7 days after incision. Animals treated with saratin will demonstrate significant increases relative to controls in the strength of the healing wounds.

Example 3

Saratin Inhibits MCP-1-Induced Human Monocyte Migration In Vitro

Monocyte Cell Isolation: Monocytes are isolated from peripheral blood mononuclear cells (PBMC). PBMCs were isolated from the buffy coats (San Diego Blood Bank) by Ficoll-Paque gradient centrifugation. Monocytes were isolated by incubating the PBMCs at $1\times10^7$ cells /mL in 100 mm petri-dish for 2 hours and collecting the adherent cells.

Monocyte Chemotaxis: Monocyte migration was quantified by blind wells Boyden chamber technique. Monocytes were suspended at $1\times10^6$ cells/mL in RPMI 1640 plus 0.5% BSA. Two hundred microliter (200 µL) wells containing various concentrations of compound (saratin) were placed in the top wells of Boyden chambers. The bottom wells of the chambers were loaded with 100 ng/mL MCP-1. An 8-µm pore polycarbonate filter was placed between the top wells and the bottom wells. Polycarbonate filters were coated with either 10 µg/mL collagen type IV, 1 mg/mL collagen type IV, 0.01 mg/mL fibronectin or 1 mg/mL fibronectin respectively overnight in 4° C. before use in the assay. The filters were also coated with 10 µg/mL or 1 mg/mL BSA. The chambers were incubated for 2 hours at 37° C., 5% $CO_2$. After incubation, the cells in the top wells were removed and the filters were then fixed by methanol and stained with Giemsa stain. Cell movement was quantified by counting the total number of cells migrating through the filters.

Results: Saratin was known to bind collagen with high affinity. Whether it also binds other extracellular matrix proteins (ECM) or general proteins such as bovine serum albumin (BSA) was not known. This issue was explored in this study. First, chemotactic filters were coated with 10 µg/mL collagen or BSA, and the migration of monocytes toward chemoattractants was examined. Results in FIG. 1A demonstrate that 100 ng/mL of MCP-1 significantly induced the chemotaxis of human monocytes (P<0.0026, as compared to cells migrating in the absence of MCP-1). Addition of 100, 10, 1 and 0.1 µg/mL of saratin inhibited MCP-1-induced monocytes migration through collagen-coated filters. The $IC_{50}$ of this inhibition was 172 pM (FIG. 1B). Saratin also inhibited MCP-1-induced monocytes chemotaxis through filters coated with 0.01 mg/mL BSA, with an $IC_{50}$ of 1.1 nM (FIG. 1C).

It is plausible that the inhibitory effect of saratin might have been due to the amount of proteins used. For example, a 10 µg/mL concentration of collagen or BSA may be too low, which might have facilitated the inhibitory effect of saratin, particularly on BSA coated filters. Therefore, we coated the filters with 1 mg/mL of collagen or BSA, and we also added another extracellular matrix, fibronectin. Similar to the results of FIG. 1, MCP-1 (100 ng/mL) was a successful chemoattractant for human monocytes migrating through filters coated with collagen, BSA or fibronectin. This activity of MCP-1 was inhibited by saratin on the three substrates. The $IC_{50}$s of this inhibition were 62.3 pM, 37 nM and 19.4 nM for cells migrating on collagen, BSA and fibronectin, respectively (FIGS. 2A, B and C). These results suggest that saratin is an inhibitor of immune cell influx and that saratin can affect the immune cell response to tissue damage.

Example 4

Saratin Inhibits MIP-1α-Induced Human T Lymphocyte Migration In Vitro

T lymphocyte Isolation: T lymphocyte populations are isolated from peripheral blood mononuclear cells (PBMC). PBMCs were isolated from the buffy coats (San Diego Blood Bank) by Ficoll-Paque gradient centrifugation. Monocytes were isolated by incubating the PBMCs at $1\times10^7$ cells /mL in 100 mm petri-dish for 2 hours and collecting the adherent cells. T lymphocytes were separated from PBMCs by the use of a Nylon Wool Column. Briefly, PBMCs were incubated over Nylon Wool Column for 1 hour at 37° C., and the non-adherent cells were rinsed from the Nylon Wool Column by RPMI complete growth medium. These cells contain about 95% T lymphocytes.

T lymphocyte Chemotaxis: T lymphocyte migration was quantified by blind wells Boyden chamber technique. T lymphocytes were suspended at $1 \times 10^6$ cells/mL in RPMI 1640 plus 0.5% BSA. Two hundred microliter (200 µL) wells containing various concentrations of compound (saratin) were placed in the top wells of Boyden chambers. The bottom wells of the chambers were loaded with 100 ng/mL MIP-1α. An 8-µm pore polycarbonate filter was placed between the top wells and the bottom wells. Polycarbonate filters were coated with either 10 µg/mL collagen type IV, 1 mg/mL collagen type IV, 0.01 mg/mL fibronectin or 1 mg/mL fibronectin respectively overnight in 4° C. before use in the assay. The filters were also coated with 10 µg/mL or 1 mg/mL BSA. The chambers were incubated for 2 hours at 37° C., 5% $CO_2$. After incubation, the cells in the top wells were removed and the filters were then fixed by methanol and stained with Giemsa stain. Cell movement was quantified by counting the total number of cells migrating through the filters.

Results. When used at 100 ng/mL, MIP-1α significantly (P<0.02) induced the chemotaxis of T lymphocytes placed on 10 µg/mL collagen-coated filters (FIG. 3A). When placed in the upper wells of the filters along with the cells, several concentrations of saratin inhibited MIP-1α-induced T lymphocyte chemotaxis. The $IC_{50}$ for inhibiting the chemotaxis on 10 µg/mL collagen-coated filters is 6.863 nM (FIG. 3B). However, no clear inhibition could be observed when 10 µg/mL BSA was used as a substrate (FIG. 3C).

We also examined the effect of saratin on the chemotaxis of T lymphocytes placed on filters coated with 1 mg/mL of collagen, BSA or fibronectin. Saratin inhibited the MIP-1α-induced chemotaxis of these cells. The $IC_{50}$s for this effect were 7.9 pM, 184.9 nM and 3.69 nM for cells migrating through 1 mg/mL collagen, BSA or fibronectin coated filters, respectively (FIGS. 4A, B and C).

Example 5

Studies for Determining the Effect of Saratin on MCP-1-Induced Migration In Vivo The effect of saratin on MCP-1-induced migration and cytokine production in vivo is determined using a mouse air pouch model.

Materials: ELISA kit for mouse TNF-α (Biosource, catalog # CMC3013), ELISA kit for mouse TGF-β (Biosource, catalog # CHC1683), ELISA kit for mouse IL-1β (Biosource, catalog # CMC0813), ELISA kit for mouse IL-8 (Biosource, catalog # CMC1063), Duoset ELISA kit for human FGF basic (R&D, catalog # DY233), Recombinant human MCP-1 (Peprotech Inc., catalog # 300-04), PBS (Mediatech, catalog # 21-031-CV)

Methods: A dorsal air pouch was created by subcutaneously injecting female BALB/c mice with 6 mL sterile air at day 0, followed 3 days latter by a second injection of 3 mL of sterile air. On day 6, 1 µg of MCP-1 in 100 µL of sterile PBS was injected into the air pouch, or in a separate injection, 100 µL PBS was used as a control. After 2 minutes, 100 µg saratin in 900 µL PBS was injected into the air pouch, 900 µL PBS as control. Two hours later, the air pouches were flushed with 1 mL PBS, the recovered volume was measured, and the number of recovered cells was determined by hemocytometer count. Supernatant of the exudates were used to assess the secretion of TNF-α, IL-1β, IL-8, TGF-β and FGF-basic according to the manufacturer's instructions.

Results: In order to demonstrate whether the activity observed in vitro might translate in vivo, the effect of saratin on the in vivo migration of cells was investigated. The air-pouch model is a well-established technique for the investigation of the migration of cells. For this study, 1 µg MCP-1 was injected into the air-pouches, and 2 hours later the cells were collected by aspiration. FIG. 5 demonstrates that administration of 1 µg MCP-1 into the mouse air pouches resulted in significant recruitment of cells into these pouches (P<0.0037, as compared to vehicle treated animals). However, administration of saratin (0.1 mg) 2 minutes after the injection of MCP-1 significantly inhibited MCP-1 recruitment of cells into the air pouches (P<0.0028).

Next, we examined the effect of saratin on the levels of cytokines accumulated in the air pouches of mouse. The levels of the pro-inflammatory and inflammatory cytokines and chemokines IL-8, TGF-β, TNF-α, IL-1β, and FGF-basic were measured. The levels of IL-8, TNF-α and IL-1β were increased after MCP-1 administration into the pouches, whereas no difference in the levels of TGF-β or FGF-basic could be observed between the control and MCP-1 treated animals (FIG. 6). The results also show that administration of 0.1 mg saratin reduced the levels of IL-8, TNF-α and IL-1β back to pre-stimulated levels, however, this reduction was not statistically significant (FIG. 6). Whereas no effect of saratin administration on FGF-basic could be demonstrated, saratin administration was associated with a significant reduction in level of TGF-β to below the basal level in the unstimulated, vehicle group (P<0.001, when compared between vehicle treated and saratin treated animals). However, the variance in the stimulated comparator group prevents us from determining if this reduction was due to the MCP-1 administration, the administration of saratin, or both.

Example 6

Studies Determining Effect of Saratin in Inflammatory Conditions

Effects of Saratin on Multiple Sclerosis

To test the effects saratin on encephalomyelitis, specifically multiple sclerosis, one or more of the compounds described herein can be administered to a murine model of experimental autoimmune encephalomyelitis (EAE), a CD4+ T-helper (Th1)-mediated, inflammatory demyelinating disease of the central nervous system (CNS) that serves as a model for multiple sclerosis.

Materials and Methods
Animals
Female SJL mice (H-2s) can be purchased from Harlan Sprague Dawley (Indianapolis, Ind.). Mice usually are 6 to 7 wk old at the initiation of the experiment.

Antigens and Antibodies

PLP 139-151 peptide (HSLGKWLGHPDKF) (SEQ ID NO: 13) can be purchased from Peptides International (Louisville, Ky.). The amino acid composition is verified by mass spectrometry, and purity (>98%) is assessed by high-performance liquid chromatography. Antibodies for use in the ELISA detection of MIP-1α, MCP-1, MIP-2, TNF-α, IL-1β, IL-8, TGF-β, FGF-2, RANTES, IL-1α, IL-2, IL-6, MIP-1β and ENA-78 are commercially available.

Priming of Donor Lymphocytes, Cell Culture, and Transfer of EAE

Donor lymphocytes are primed by subcutaneous immunization of normal SJL/J mice with 25 μg of PLP139-151 in CFA containing 4 mg/mL of Mycobacterium tuberculosis (Difco, Detroit, Mich.). Seven days later, draining lymph node cells are pooled and cultured in vitro in complete Dulbecco's minimum essential medium (Biowhitaker, Bethesda, Md.) containing $5 \times 10^{-5}$ M 2-ME (GIBCO), 2 mM L-glutamine (GIBCO), 100 U/mL of penicillin (GIBCO), 100 μg/mL of streptomycin (GIBCO), 0.1 mM nonessential amino acids (GIBCO), and 5% fetal calf serum (Hy-Clone) at a concentration of $6 \times 10^6$ cells/mL in the presence of 50 μg/mL of PLP 139-151 for 72 hr. The cells are harvested and washed, and $3 \times 10^6$ viable T lymphocyte blasts are transferred intraperitoneally to normal SJL/J recipients. After cell transfer, mice are evaluated for the development of EAE.

Cytokines ELISA

Assessment of MIP-1α, MCP-1, MIP-2, TNF-α, IL-1β, IL-8, TGF-β, FGF-2, RANTES, IL-1α, IL-2, IL-6, MIP-1β and ENA-78, as well as other chemokines, can be quantified from tissue samples and culture supernatants using ELISA. Spinal cord samples are homogenized in 1 mL of phosphate-buffered saline and clarified by centrifugation (400×g) for 10 min. ELISA plates are coated with 2 μg/mL of capture antibody diluted in PBS and coated overnight at 4° C. Samples are diluted in blocking buffer and incubated in ELISA plates for 2 hours at room temperature. Alkaline phosphatase-conjugated secondary antibodies are used as detection reagents. Cytokines concentrations are determined by constructing a standard curve of known values and calculating the picogram/milliliter of chemokines in samples.

Clinical Evaluation

Adoptive R-EAE is induced by the transfer of $3 \times 10^6$ in vitro-stimulated PLP139-151-specific T lymphocyte blasts from PLP 139-151 peptide-primed mice. Individual animals are observed daily and graded according to their clinical severity as follows: 0=no abnormality; 1=limp tail; 2=limp tail and partial hind limb weakness (waddling gait); 3=complete hind limb paralysis; and 4=death. In most experiments, there is a range of maximum severity between grades 1 and 3. Mice rarely die from EAE; however, the score of 4 is used when no other cause could be attributed to a death. A relapse is scored when a mouse developed additional neurological deficits (an increase of at least one clinical grade) after a period of stabilization or improvement.

Using the methods described above it can be determined whether treatment with saratin blocks or improves EAE in mice, or change cytokine concentration in samples produced. This can demonstrate the effectiveness of saratin in the treatment of this disease.

Effect of Saratin on Asthma

To test the effects of saratin on asthma one or more of the compounds described herein can be administered to a murine model of asthma, such as OVA-immunized BALB/c mice, or mice with α-GalCer induced airway hyperresponsiveness (AHR).

Materials and Methods

Animals. BALB/cByJ mice can be obtained from the Jackson Laboratory, Bar Harbor, Md.

Monoclonal Antibodies: Monoclonal antibodies can be purified from ascites by ammonium sulfate precipitation and ion-exchange chromatography. The following hybridomas can be used: R46A2 (anti-IFN-γ mAb) XMG1.2 (anti-IFN-γ antibody); BVD4-1D11, BVD6-24G2 (anti-IL-4 mAb). These hybridomas can be obtained from ATCC (American Type Culture Collection, Rockville, Md.). Anti-38C13 idiotype mAb 4G10 (rat IgG2a) can be used as isotype control.

Immunizations. BALB/c mice can be primed in the footpads with OVA (100 μg/mouse) adsorbed to 200 μg of alum ($Al[OH]_3$). Mice can be challenged with 50 μg OVA in 50 μl NaCl 0.9% intranasally 7, 8, and 9 days later. One day after the last intranasal challenge with OVA, airway hyperreactivity can be measured from conscious mice after inhalation of increasing concentrations of methacholine in a whole body plethysmograph. Immunization with α-GalCer can be performed as described.

To facilitate pulmonary aspiration during intranasal administration of antigen, mice can be lightly anesthetized by intraperitoneal (i.p.) injection with 0.25 mL of ketamine (0.44 mg/mL)/xylazine (6.3 mg/mL) in normal saline. Usually, 75% of the intranasally administered antigen can be subsequently detected in the lungs (J. Exp. Med. 1997; 185:1671-9).

Cytokine ELISA. ELISAS can be performed as previously described above. The antibody pairs used can be as follows, listed by capture/biotinylated detection: IL-4, BVD4-1D11/BVD6-24G2; IFN-γ, R4-6A2/XMG1.2. Recombinant cytokine can be used as standards, with curves generated in 1:2 dilutions from 500 to 39 pg/mL for IL-4, and 20-2, 156 ng/mL for IFN-γ.

Measurement of anti-OVA antibody isotypes: Mice can be bled at the time of sacrifice and OVA-specific antibody can be measured using a modified antigen-specific ELISA. For measurement of OVA specific IgG, plates can be coated overnight with 5 μg/mL OVA. After washing and blocking, serial diluted sera can be added to the plates. Following overnight incubation, the plates can be developed using HRPO-conjugated goat anti-IgG subclass-specific antibodies (Southern Biotechnology Associates, Birmingham, Ala.). After additional washing, OPD substrate can be added, the plates developed and the OD can be determined at 492 nm. Anti-OVA IgG1 mAb 6C1 and anti-OVA IgG2a mAb 3A11 can be used as standards for quantitation of each IgG subclass. Determination of OVA-specific IgE can be performed by ELISA, using rat anti-mouse IgE mAb EM95 (5.0 μg/ml) to coat plates. After the samples are applied and incubated overnight, plates are washed and biotinylated OVA (10 μg/mL) can be added. Two hours later, plates are washed and HRPO-conjugated streptavidin (Southern Biotechnology Associates) can be added. Plates can be developed with OPD substrate and the OD determined at 492 nm. Sera from mice hyperimmunized with OVA in alum can be quantified for IgE and used as standard for the OVA-specific IgE ELISA.

Measurement of Airway Responsiveness: Airway responsiveness can be assessed by methacholine-induced airflow obstruction from conscious mice placed in a whole body plethysmograph (model PLY 3211, Buxco Electronics Inc., Troy, N.Y.). Pulmonary airflow obstruction can be measured by Penh using the following formula:

$$Penh = \left(\frac{Te}{RT} - 1\right) \times \left(\frac{PEF}{PIF}\right),$$

where Penh = enhanced pause (dimensionless),

Te = expiratory time,

RT = relaxation time,

PEF=peak expiratory flow (mL/s), and PIF=peak inspiratory flow (mL/s) (Am. J. Respir. Crit. Care Med., 1997; 156:766-75). Enhanced pause (Penh), minute volume, tidal volume, and breathing frequency can be obtained from chamber pressure, measured with a transducer (model TRD5100) connected to preamplifier modules (model MAX2270) and analyzed by system XA software (model SFT 1810). Measurements of methacholine responsiveness can be obtained by exposing mice for 2 min to NaCl 0.9%.

Collection of BAL Fluid and Lung Histology: Animals can be injected i.p. with a lethal dose of phenobarbital (450 mg/kg). The trachea is cannulated, and the lung is then lavaged with 0.8 mL of PBS three times, and the fluid pooled. Cells in the lavage fluid can be counted using a hemocytometer and BAL cell differentials can be determined on slide preparations stained with Hansel Stain (Lide Laboratories, Florissant, Mo.). At least 200 cells can be differentiated by light microscopy based on conventional morphologic criteria. In some animals, no BAL is performed but lungs are removed, washed with PBS, fixed in 10% formalin and stained with hematoxylin and eosin.

Using the methods described above it can be determined whether treatment with saratin blocks α-GalCer induced AHR, reduces OVA/alum induced AHR, or changes cytokine concentration in serum produced following α-GalCer induced AHR. This can demonstrate the effectiveness of saratin in the treatment of this disease.

Example 7

Manufacture of Saratin

Examples for the manufacture of saratin are described in U.S. Pat. Nos. 6,774,107 and 6,881,722. In the studies described herein hydrophobic interaction chromatography (HIC) is described as an alternative step to reduce a proteolytic activity present in the culture supernatant as described in Table 3. In this procedure, in the seed cultivation step, sample of yeasts are grown in shake flask and the cultures are observed for contaminants. Then main fermentation step takes places as described in U.S. Pat. Nos. 6,774,107 and 6,881,722. The supernatants are removed and separated from cells as described in the Cell separation step of table 3. To further remove particulates and cell debris from the supernatant, the supernatants are filtrated as described in the filtration step of Table 3. After the filtration step the supernatants are directly loaded into the HIC (no need to exchange buffer). HIC removes proteases present in the supernatant making no longer necessary the addition of heat shock proteins as described in U.S. Pat. Nos. 6,774,107 and 6,881,722. The flow through from the HIC is then diluted 1:1 with DEAE loading buffer and then loaded into a DEAE column. The DEAE column is washed and then eluted with a linear gradient as described in U.S. Pat. Nos. 6,774,107 and 6,881,722. The captured fraction with at least 90% purity are recombined and filtered as described in the Diafiltration and filtration steps of table 3. Saratin is then diluted in the appropriate vehicle to the desired concentration.

TABLE 3

Outline of Planned GMP Process for Saratin

| Planned GMP Process | Remarks |
| --- | --- |
| Seed Cultivation | shake flasks |
| Main Fermentation (Fed Batch) | as U.S. Pat. No. 6,774,107, 50 L scale, prior to harvesting chilling of culture to 15° C. inside fermentor |
| Cell Separation (Centrifugation) | Batch centrifugation at 10° C., 6L per run, 2 runs, duration 1 h |
| Filtration | bioburden reduction, 10 L filtrate, duration 0.25 h, at this point not less than 2.5 g saratin total |
| HIC, non binding | loading at 150 ml/min, duration 1.5 hours (probably higher flow rates possible) |
| Dilution | addition of one part DEAE buffer A |
| Product Purification (IEC) | sample loading over night at room temperature, 400 to 500 ml column, gradient elution as U.S. Pat. No. 6,774,107 next day probably intermediate storage at 2-8° C. during IPC |
| Diafiltration (TFF) 0.2 μm Filtration | 5 kDa ultracell membrane, 0.1 m² area, duration 2 h |
| Bulk (API) | storage at 2-8° C. in PETG bottles |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating surgically-induced inflammation or a surgically-induced adhesion arising from tendon reconstructive surgery comprising locally administering at the site of the tendon reconstructive surgery an effective amount of saratin.

2. The method of claim 1, wherein saratin is administered along the entire length of the exposed tendon.

3. The method of claim 1, wherein saratin is administered at the interface of the suture connecting severed tendon ends.

* * * * *

SEQUENCE LISTING

<160> NUMBER OF SEQ ID NOS: 13

<210> SEQ ID NO 1
<211> LENGTH: 375
<212> TYPE: DNA
<213> ORGANISM: Hirudo medicinalis
<220> FEATURE:
<221> NAME/KEY: CDS
<222> LOCATION: (64)..(372)

<400> SEQUENCE: 1

```
atgaagtatt tcttgatttc cttcctttgc ctcgcaagct tgctgatctc aactacttct      60 tca gaa gaa cgt gaa gat tgt tgg acg ttt tac gcg aac aga aaa tat     108
    Glu Glu Arg Glu Asp Cys Trp Thr Phe Tyr Ala Asn Arg Lys Tyr
    1               5                   10                  15 aca gac ttc gat aaa tct ttt aag aag tcc tct gat ctt gac gaa tgc     156
Thr Asp Phe Asp Lys Ser Phe Lys Lys Ser Ser Asp Leu Asp Glu Cys
             20                  25                  30 aaa aaa aca tgt ttc aag acg gag tac tgc tac atc gtt ttt gaa gac     204
Lys Lys Thr Cys Phe Lys Thr Glu Tyr Cys Tyr Ile Val Phe Glu Asp
             35                  40                  45 acg gtc aac aag gaa tgt tac tac aat gtc gtt gat ggt gaa gag tta     252
Thr Val Asn Lys Glu Cys Tyr Tyr Asn Val Val Asp Gly Glu Glu Leu
         50                  55                  60 gac caa gaa aaa ttt gtt gtc gac gaa aac ttc acg gaa aat tat ttg     300
Asp Gln Glu Lys Phe Val Val Asp Glu Asn Phe Thr Glu Asn Tyr Leu
     65                  70                  75 aca gac tgc gag ggt aaa gat gca ggt aat gcg gca ggt aca ggt gac     348
Thr Asp Cys Glu Gly Lys Asp Ala Gly Asn Ala Ala Gly Thr Gly Asp
 80                  85                  90                  95 gag tca gat gaa gtt gat gaa gat taa                                  375
Glu Ser Asp Glu Val Asp Glu Asp
                 100
```

<210> SEQ ID NO 2
<211> LENGTH: 103
<212> TYPE: PRT
<213> ORGANISM: Hirudo medicinalis

<400> SEQUENCE: 2

```
Glu Glu Arg Glu Asp Cys Trp Thr Phe Tyr Ala Asn Arg Lys Tyr Thr
1               5                   10                  15

Asp Phe Asp Lys Ser Phe Lys Lys Ser Ser Asp Leu Asp Glu Cys Lys
            20                  25                  30

Lys Thr Cys Phe Lys Thr Glu Tyr Cys Tyr Ile Val Phe Glu Asp Thr
        35                  40                  45

Val Asn Lys Glu Cys Tyr Tyr Asn Val Val Asp Gly Glu Glu Leu Asp
    50                  55                  60

Gln Glu Lys Phe Val Val Asp Glu Asn Phe Thr Glu Asn Tyr Leu Thr
65                  70                  75                  80

Asp Cys Glu Gly Lys Asp Ala Gly Asn Ala Ala Gly Thr Gly Asp Glu
                85                  90                  95

Ser Asp Glu Val Asp Glu Asp
            100
```

<210> SEQ ID NO 3
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<221> NAME/KEY: modified_base
<222> LOCATION: (9)
<223> OTHER INFORMATION: a, c, g or t

<400> SEQUENCE: 3
gargarmgng argaytgttg gac                                           23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)
<223> OTHER INFORMATION: a, c, g or t

<400> SEQUENCE: 4
gargarmgng argaytgctg gac                                           23

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcatcgatgg aagaacgtga agac                                          24

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tagcgctttt gacgtcgtcg tca                                           23

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaagaatgca aggatgagga ttattg                                        26

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
```

-continued

```
aagcttctag tcttcgtcaa cttcg                                              25

<210> SEQ ID NO 9
<211> LENGTH: 94
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cggatccatg aaattcttag tcaacgttgc ccttgttttt atggtcgtat acatttctta        60
catctatgcg gaagaacgtg aagattgttg gact                                    94

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggtacctcac atatcttcat caac                                               24

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcatgcggcc gcctaatctt catcaacttc                                         30

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcatgaattc gaagaacgtg aagattg                                            27

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

His Ser Leu Gly Lys Trp Leu Gly His Pro Asp Lys Phe
 1               5                  10
```